(12) United States Patent
Cheung et al.

(10) Patent No.: US 9,227,982 B2
(45) Date of Patent: Jan. 5, 2016

(54) 4-OXO-3,5,7,8-TETRAHYDRO-4H-PYRANO[4,3-D]PYRMINIDINYL COMPOUNDS FOR USE AS TANKYRASE INHIBITORS

(75) Inventors: Atwood Kim Cheung, Cambridge, MA (US); Donovan Noel Chin, Cambridge, MA (US); Jianmei Fan, Cambridge, MA (US); Michael David Shultz, Cambridge, MA (US); Ronald Charles Tomlinson, Sudbury, MA (US)

(73) Assignee: NOVARTIS AG, Basel (CH)

( * ) Notice: Subject to any disclaimer, the term of this patent is extended or adjusted under 35 U.S.C. 154(b) by 61 days.

(21) Appl. No.: 14/154,170

(22) PCT Filed: Jul. 13, 2012

(86) PCT No.: PCT/US2012/046699
§ 371 (c)(1),
(2), (4) Date: May 22, 2014

(87) PCT Pub. No.: WO2013/010092
PCT Pub. Date: Jan. 17, 2013

(65) Prior Publication Data
US 2015/0210709 A1 Jul. 30, 2015

Related U.S. Application Data

(60) Provisional application No. 61/507,313, filed on Jul. 13, 2011.

(30) Foreign Application Priority Data

Jul. 13, 2012 (WO) ................ PCT/US2012/046699

(51) Int. Cl.
*A01N 43/90* (2006.01)
*A61K 31/519* (2006.01)
*C07D 491/00* (2006.01)
*C07D 495/00* (2006.01)
*C07D 491/052* (2006.01)

(52) U.S. Cl.
CPC .......... *C07D 491/052* (2013.01); *A61K 31/519* (2013.01)

(58) Field of Classification Search
None
See application file for complete search history.

(56) References Cited

U.S. PATENT DOCUMENTS

| | | |
|---|---|---|
| 2004/0132718 A1 | 7/2004 | Jacobson et al. |
| 2005/0075347 A1 | 4/2005 | Albrecht et al. |
| 2005/0085476 A1 | 4/2005 | Seko et al. |
| 2005/0159431 A1 | 7/2005 | Albrecht et al. |
| 2008/0269234 A1 | 10/2008 | Gandhi et al. |
| 2009/0163545 A1 | 6/2009 | Goldfarb |

FOREIGN PATENT DOCUMENTS

| | | |
|---|---|---|
| EP | 1 142 881 A1 | 10/2001 |
| EP | 1 396 488 A1 | 3/2004 |
| WO | 99/011624 A1 | 3/1999 |
| WO | 02/048117 A1 | 6/2002 |
| WO | 02/094790 A1 | 11/2002 |
| WO | 03/049678 A2 | 6/2003 |
| WO | 03/063874 A1 | 8/2003 |
| WO | 03/080581 A1 | 10/2003 |
| WO | 2004/087677 A2 | 10/2004 |
| WO | 2004/111014 A1 | 12/2004 |
| WO | 2005/018557 A2 | 3/2005 |
| WO | 2005/061460 A1 | 7/2005 |
| WO | 2006/003146 A1 | 1/2006 |
| WO | 2006/004925 A1 | 1/2006 |
| WO | 2007/002701 A2 | 1/2007 |
| WO | 2007/127726 A2 | 11/2007 |
| WO | 2009/059994 A2 | 5/2009 |
| WO | 2009/061131 A2 | 5/2009 |
| WO | 2009/118382 A1 | 10/2009 |

OTHER PUBLICATIONS

Bae et al., Tankyrase 1 interacts with Mcl-1 proteins and inhibits their regulation of apoptosis. J Biol Chem. Feb. 14, 2003;278(7):5195-204. Epub Dec. 9, 2002.
Barker et al., Mining the Wnt pathway for cancer therapeutics. Nat Rev Drug Discov. Dec. 2006;5(12):997-1014. Review.
Behrens et al., Functional interaction of an axin homolog, conductin, with beta-catenin, APC, and GSK3beta. Science. Apr. 24, 1998;280(5363):596-9.
Chang et al., Poly(ADP-ribose) is required for spindle assembly and structure. Nature. Dec. 2, 2004;432(7017):645-9.
Chang et al., NuMA is a major acceptor of poly(ADP-ribosyl)ation by tankyrase 1 in mitosis. Biochem J. Oct. 15, 2005;391(Pt 2):177-84.
Chi et al., Tankyrase is a golgi-associated mitogen-activated protein kinase substrate that interacts with IRAP in GLUT4 vesicles. J Biol Chem. Dec. 8, 2000;275(49):38437-44.

(Continued)

*Primary Examiner* — Jeffrey H Murray
(74) *Attorney, Agent, or Firm* — Qian Zhang

(57) ABSTRACT

The present invention provides for compounds of formula (I)

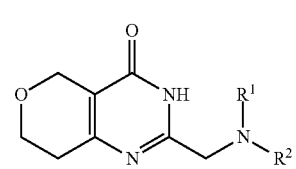

(I)

wherein $R^1$ and $R^2$ are defined herein. The present invention also provides for pharmaceutical compositions and combinations comprising a compound of formula (I) as well as for the use of such compounds as tankyrase inhibitors and in the treatment of Wnt signaling and tankyrase 1 and 2 signaling related disorders which include, but are not limited to, cancer.

13 Claims, No Drawings

(56) References Cited

OTHER PUBLICATIONS

Clevers, Wnt/beta-catenin signaling in development and disease. Cell. Nov. 3, 2003;127(3):469-80.

Cook et al., Role for the related poly(ADP-Ribose) polymerases tankyrase 1 and 2 at human telomeres. Mol Cell Biol. Jan. 2002;22(1):332-42.

Dynek et al., Resolution of sister telomere association is required for progression through mitosis. Science. Apr. 2, 2004;304(5667):97-100.

Fancy et al., Axing as regulatory and therapeutic target in newborn brain injury and remyelination. Nat Neurosci. Jun. 26, 2011;14(8):1009-16.

Hahn et al. Inhibition of telomerase limits the growth of human cancer cells. Nat Med. 1999;5(10):1164-70.

Hart et al., Downregulation of beta-catenin by human Axin and its association with the APC tumor suppressor, beta-catenin and GSK3 beta. Curr Biol. May 7, 1998;8(10):573-81.

Huang et al., Tankyrase inhibition stabilizes axin and antagonizes Wnt signalling. Nature. Oct. 1, 2009;461(7264):614-20.

Kishida et al., Axin prevents Wnt-3a-induced accumulation of beta-catenin. Oncogene. Jan. 28, 1999;18(4):979-85.

Kwon et al., Mechanisms to suppress multipolar divisions in cancer cells with extra centrosomes. Genes Dev. Aug. 15, 2008;22(16):2189-203.

Lammi et al., Mutations in AXIN2 cause familial tooth agenesis and predispose to colorectal cancer. Am J Hum Genet. May 2004;74(5):1043-60. Epub Mar. 23, 2004.

Lee et al., The roles of APC and Axin derived from experimental and theoretical analysis of the Wnt pathway. PLoS Biol. Oct. 2003;1(1):E10. Epub Oct. 13, 2003.

Li et al., Herpes simplex virus requires poly(ADP-ribose) polymerase activity for efficient replication and induces extracellular signal-related kinase-dependent phosphorylation and ICP0-dependent nuclear localization of tankyrase 1. J Virol. Jan. 2012;86(1):492-503. Epub Oct. 19, 2011.

Liu et al., Efficient total synthesis of (S)-14-azacamptothecin. Chem Asian J. Jun. 1, 2010;5(6):1382-8.

Liu et al., Mutations in AXIN2 cause colorectal cancer with defective mismatch repair by activating beta-catenin/TCF signalling. Nat Genet. Oct. 2000;26(2):146-7.

Miyaki et al., Characteristics of somatic mutation of the adenomatous polyposis coli gene in colorectal tumors. Cancer Res. Jun. 1, 1994;54(11):3011-20.

Miyoshi et al., Somatic mutations of the APC gene in colorectal tumors: mutation cluster region in the APC gene. Hum Mol Genet. Jul. 1992;1(4):229-33.

Polakis, The many ways of Wnt in cancer. Curr Opin Genet Dev. Feb. 2007;17(1):45-51.

Powell et al., APC mutations occur early during colorectal tumorigenesis. Nature. Sep. 17, 1992;359(6392):235-7.

Salic et al., Control of beta-catenin stability: reconstitution of the cytoplasmic steps of the wnt pathway in Xenopus egg extracts. Mol Cell. Mar. 2002;5(3):523-32.

Seimiya et al., Tankyrase 1 as a target for telomere-directed molecular cancer therapeutics. Cancer Cell. Jan. 2005;7(1):25-37.

Smith et al., Tankyrase, a poly(ADP-ribose) polymerase at human telomeres. Science. Nov. 20, 1998;282(5393):1484-7.

Taniguchi et al., Mutational spectrum of beta-catenin, AXIN1, and AXIN2 in hepatocellular carcinomas and hepatoblastomas. Oncogene. Jul. 18, 2002;21(31):4863-71.

Ulsamer et al., Axin pathway activity regulates in vivo pY654-β-catenin accumulation and pulmonary fibrosis. J Biol Chem. Feb. 10, 2012;287(7):5164-72.

Yeh et al., Hypermetabolism, hyperphagia, and reduced adiposity in tankyrase-deficient mice. Diabetes. Nov. 2009;58(11):2476-85.

4-OXO-3,5,7,8-TETRAHYDRO-4H-PYRANO[4,3-D]PYRMINIDINYL COMPOUNDS FOR USE AS TANKYRASE INHIBITORS

FIELD OF THE INVENTION

The present invention relates to novel 4-oxo-3,5,7,8-tetrahydro-4H-pyrano[4,3-d]pyrimidinyl compounds, pharmaceutical compositions containing them, and the use of such compounds as tankyrase inhibitors and in the treatment of Wnt signaling and tankyrase 1 and 2 signaling related disorders which include, but are not limited to, cancer.

BACKGROUND OF THE INVENTION

The evolutionarily conserved canonical Wnt/β-catenin signal transduction cascade controls many aspects of metazoan development. Context-dependent activation of the pathway is involved in embryonic cell fate decisions, stem cell regulation and tissue homeostasis (Clevers, H. *Cell* 2006, 127, 469-80).

A key feature of the Wnt/β-catenin pathway is the regulated proteolysis of the downstream effector β-catenin by the β-catenin destruction complex. The principal constituents of the β-catenin destruction complex are adenomatous polyposis coli (APC), Axin, and GSK3α/β. In the absence of Wnt pathway activation, cytosolic β-catenin is constitutively phosphorylated and targeted for degradation. Upon Wnt stimulation, the β-catenin destruction complex disassociates, which leads to the accumulation of nuclear β-catenin and transcription of Wnt pathway responsive genes.

Inappropriate activation of the pathway, mediated by over expression of Wnt proteins or mutations affecting components of the β-catenin destruction complex, thus leading to stabilization of β-catenin, has been observed in many cancers. Notably, truncating mutations of the tumour suppressor APC are the most prevalent genetic alterations in colorectal carcinomas (Miyaki, M. et al. *Cancer Res* 1994, 54, 3011-20; Miyoshi, Y. et al. *Hum Mol Genet* 1992, 1, 229-33; and Powell, S. M. et al. *Nature* 1992, 359, 235-7). In addition, Axin1 and Axin2 mutations have been identified in patients with hepatocarcinomas and colorectal cancer respectively (Taniguchi, K. et al. Oncogene 2002, 21, 4863-71; Liu, W. et al. *Nat Genet* 2000, 26, 146-7; Lammi, L. et al. *Am J Hum Genet* 2004, 74, 1043-50). These somatic mutations result in Wnt-independent stabilization of β-catenin and constitutive activation of β-catenin-mediated transcription.

Deregulated Wnt pathway activity has also been implicated in many other cancers (Polakis, P. *Curr Opin Genet Dev* 2007, 17, 45-51; and Barker, N. et al. *Nat Rev Drug Discov* 2006, 5, 997-1014), including colorectal, melanoma, breast, liver, lung and gastric cancers. Other disorders associated with aberrant Wnt signaling include osteoporosis, osteoarthritis, polycystic kidney disease, pulmonary fibrosis, diabetes, schizophrenia, vascular disease, cardiac disease, non-oncogenic proliferative diseases, and neurodegenerative diseases such as Alzheimer's disease.

The efficient assembly of the multi-protein β-catenin destruction complex is dependent on the steady state levels of its principal constituents. Axin has been reported to be the concentration-limiting factor in regulating the efficiency of the β-catenin destruction complex (Salic, A., et al. *Mol Cell* 2000, 5, 523-32; and Lee, E. et al. *PLoS Biol* 2003, 1, E10) and increased expression of Axin can enhance β-catenin degradation in cell lines expressing truncated APC (Behrens, J. et al. *Science* 1998, 280, 596-9; Kishida, M. et al. *Oncogene* 1999, 18, 979-85; and Hart, M. J., et al. *Curr Biol* 1998, 8, 573-81). Thus, it is likely that Axin protein levels need to be tightly regulated to ensure proper Wnt pathway signaling.

It has recently been found that β-catenin degradation can be promoted by stablising Axin through the inhibition of the poly-ADP-ribose polymerase (PARP) enzymes tankyrase 1 and tankyrase 2, as explained in WO 2009/059994 and Huang et al., (Huang, S. M., et al. *Nature* 2009, 461, 614-620). Both tankyrase isoforms interact with a highly conserved domain of Axin and stimulate its degradation through the ubiquitin-proteasome pathway. This previously unknown mechanism for stabilising Axin protein, thereby enhancing β-catenin degradation, can be exploited for treating Wnt signaling-related disorders. Axin proteins are essential regulators of a spectrum of physiological processes, including brain oligodendrocyte progenitor cell differentiation for remyelination (Fancy, S., et al. *Nature NeuroSci* 2011, 14, 1009-1017), and epithelial-to-mesenchymal transition during pulmonary fibrosis (Ulsamer, A., et al. *J Bio Chem* 2012, 287, 5164-5172). Thus, by way of stabilizing Axin proteins, Tankyrase inhibitors could be used as a therapy for remyelination post brain injury and pulmonary fibrosis.

Tankyrase has several binding protein partners, including TRF1, a double-stranded telomeric repeat binding protein (Smith, S., et al. *Science* 1998, 282, 1484-1487); NuMA, an essential protein in mitotic spindle assembly (Chang, W., et al. *Biochem J,* 2005, 391, 177-184); IRAP, an integral membrane protein involved in glucose uptake in response to insulin (Chi, N. W., et al. *J Biol Chem* 2000, 275, 38437-38444); and Mcl-1, a pro-apoptotic protein (Bae, J., et al. *J Biol Chem* 2003, 278, 5195-5204).

By way of its various interacting proteins, tankyrase proteins have been implicated in different biological functions. Tankyrase poly (ADP-ribosyl)ates TRF1, releasing it from telomeres and enhancing telomere access to telomerase. Thus, tankyrase functions as a positive regulator for telomere elongation by telomerase, supported by the findings that long-term overexpression of tankyrase leads to telomere elongation (Cook, B. D., et al *Mol Cell Biol* 2002, 22, 332-242). Telomere maintenance by telomerase has been attributed to the uncontrolled proliferation of cancer cells (Hahn, W. C., et al, *Nat Med* 1999, 5, 1164-1169). Tankyrase could be a target for cancer therapy by inhibiting the telomere accessibility for telomerase. Tankyrase inhibition could be used as an effective cancer therapy to treat patients with a wide spectrum of cancers, including leukemia, lymphoma, multiple myeloma, lung, and breast cancer.

Tankyrase also plays a role in cell mitosis by: 1) poly(ADP-ribosyl)ating NuMA during mitosis and regulating its functions at spindle poles (Chang, W., et al. *Biochem J* 2005, 391, 177-184); 2) by regulating spindle assembly and structure (Chang, P., et al. *Nature* 2004, 432, 645-649); and 3) by maintaining sister chromatid resolution at telomeres (Dynek, J., et al. *Science* 2004, 304, 97-100). Inhibition of tankyrase leads to cell mitotic arrest or senescence, and thus could be exploited for treating diseases that have abnormal mitotic division, such as cancer. Examples include breast, lung, ovarian, leukemia, lymphoma, and melanoma. In addition, tankyrase 1 was identified as a gene required for centrosome clustering, a mechanism that cancer cells with supernumerary centrosomes employs to suppress multipolar mitosis and enable bipolar mitosis (Kwon, M., et al. *Genes Dev* 2008, 22, 2189-2203). Thus inhibition of tankyrase could be exploited for treating cancers with centrosome amplification, including both solid and haematological cancers, examples include breast, bladder, lung, colon, and leukemia.

Moreover, One of the cellular localizations of tankyrase is at the Golgi apparatus co-localizing with the glucose transporter GLUT4 vesicles where tankyrase is associated with IRAP, and tankyrase is implicated in the regulation of GLUT4 trafficking in adipocytes (Chi, N. W., et al. *J Biol Chem* 2000, 275, 38437-38444). Tankyrase-deficient mice exhibit reduced adiposity and increased energy expenditure by increases in both fatty acid oxidation and insulin-stimulated glucose utilization (Yeh, T., et al. *Diabetes* 2009). This supports tankyrase involvement in energy homeostasis in mammals and inhibiting tankyrase can be exploited for treating metabolic diseases, such as obesity.

Tankyrase has been repoted to be a host protein targeted by Herpes Simplex Virus (HSV), modulated by HSV through hyperphosphorylation, nuclear transport and proteasomal degradation (Li Z., et al. *J of Virol* 2012, 86, 492-503). More importantly, efficient HSV viral replication requires the enzymatic activity of tankyrase proteins. Inhibition of tankyrase activity by inhibitor XAV939 (WO 2009/059994, Huang, S. M., et al. *Nature* 2009, 461, 614-620) suppressed HSV viral protein expression and decreased viral growth. Thus, inhibition of tankyrase can be exploited as anti-viral therapeutics, including but not limited to treatment of HSV infection.

Consequently, compounds that inhibit tankyrase (TNKS) and/or Wnt Signaling may be useful for treatment of diseases mediated by such inhibitions.

SUMMARY OF THE INVENTION

The present invention provides for compounds of formula (I):

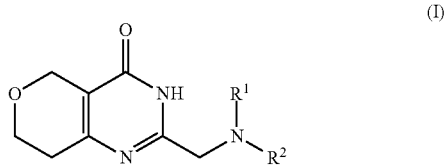

(I)

wherein $R^1$ and $R^2$ are defined herein. The present invention also provides for pharmaceutical compositions and combinations comprising a compound of formula (I) as well as for the use of such compounds as tankyrase inhibitors and in the treatment of Wnt signaling and tankyrase 1 and 2 signaling related disorders which include, but are not limited to, cancer.

DETAILED DESCRIPTION OF THE INVENTION

The present invention provides for compounds of formula (I)

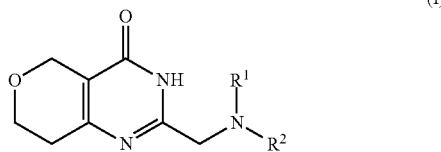

(I)

wherein:
$R^1$ is hydrogen or $C_{1-4}$ haloalkyl, or $C_{1-4}$ alkyl optionally substituted with one substituent selected from the group consisting of: hydroxy, cyano, $C(O)R^a$, $C_{3-5}$ cycloalkyl, optionally substituted phenyl, and optionally substituted 5-6 membered heteroaryl, wherein said phenyl and 5-6 membered heteroaryl are each optionally substituted with one or two substituents each independently selected from the group consisting of: halo, hydroxy, $C_{1-3}$ alkyl, $C_{1-3}$ alkoxy, and cyano;
$R^2$ is $R^3$—$C_{1-2}$alkylene-C(O)—, $R^3$—$C_{1-2}$alkylene-S(O)$_2$—, or $R^3$—$C_{1-2}$alkylene-COO—;
$R^3$ is optionally substituted phenyl, optionally substituted 6 membered heteroaryl, or optionally substituted indolyl,
wherein said phenyl, heteroaryl and indolyl are each optionally substituted with one to three substitutents each independently selected from the group consisting of: halo, hydroxy, cyano, nitro, $C_{1-6}$ alkyl, $C_{1-6}$ alkoxy, $C_{1-6}$ haloalkyl, $C(O)R^a$, $COOR^a$, $NR^aR^b$, $NHC(O)R^a$, and $C(O)NR^aR^b$;
$R^a$ is H or $C_{1-6}$ alkyl; and
$R^b$ is H or $C_{1-6}$ alkyl.

As used herein, the term "alkyl" refers to a fully saturated branched or unbranched hydrocarbon moiety having up to 6 carbon atoms. Alkyl groups may be optionally substituted with one or more substituents as defined. Unless otherwise provided, alkyl refers to hydrocarbon moieties having 1 to 6, 1 to 4, or 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

As used herein, the term "alkylene" refers to divalent alkyl group as defined herein above having 1 to 2 carbon atoms. Representative examples of alkylene include, methylene and ethylene.

As used herein, the term "alkoxy" refers to alkyl-O—, wherein alkyl is defined herein above. Typically, alkoxy groups have 1 to 6 or 1 to 3 carbon atoms. Representative examples of alkoxy include, but are not limited to, methoxy, ethoxy, propoxy, 2-propoxy, butoxy, tert-butoxy, pentyloxy, hexyloxy, As used herein, the term "$C_{3-5}$ cycloalkyl" refers to a saturated monocyclic hydrocarbon group of 3-5 carbon atoms. Examples of cycloalkyl groups are cyclopropyl, cyclobutyl and cyclopentyl.

As used herein, the term "halo" refers to fluorine, bromine, chlorine or iodine, in particular fluorine or chlorine. Halogen-substituted groups and moieties, such as alkyl substituted by halogen (haloalkyl) can be mono-, poly- or per-halogenated.

As used herein, the term "haloalkyl" refers to an alkyl as defined herein, which is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms.

As used herein, the term "heteroatoms" refers to nitrogen (N), oxygen (O) or sulfur (S) atoms, in particular nitrogen or oxygen.

As used herein, the term "heteroaryl" refers to a 5 or 6 membered monocyclic ring system, having 1 to 4 heteroatoms. Heteroaryl groups containing more than one heteroatom may contain different heteroatoms. Heteroaryl groups may be optionally substituted with one or more substituents as defined herein. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, furazanyl, thiadiazolyl, tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

When any group or moiety, such as alkyl, heteroaryl, or phenyl, is defined herein as being "optionally substituted with one, one or two, or one to three substituents each independently selected from the group consisting of" it is understood that the group or moiety is unsubstituted or substituted with one, one or two, or one to three substituents, wherein each substituent is independently selected from the recited group of substituents.

The skilled artisan will appreciate that salts, including pharmaceutically acceptable salts, of the compounds according to formula (I) may be prepared. These salts may be prepared in situ during the final isolation and purification of the compound, or by separately reacting the purified compound in its free acid or free base form with a suitable base or acid, respectively.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Solvates, including pharmaceutically acceptable solvates, of the compounds of formula (I) may also be prepared. "Solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

As used herein, the term "pharmaceutically acceptable" means a compound which is suitable for pharmaceutical use. Salts and solvates (e.g. hydrates and hydrates of salts) of compounds of the invention which are suitable for use in medicine are those where in the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their pharmaceutically acceptable salts and solvates.

The compounds of formula (I), including salts and solvates thereof, may exist in crystalline forms, non-crystalline forms, or mixtures thereof. The compound or salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I).

The invention also includes various isomers of the compounds of formula (I). "Isomer" refers to compounds that have the same composition and molecular weight but differ in physical and/or chemical properties. The structural difference may be in constitution (geometric isomers) or in the ability to rotate the plane of polarized light (stereosiomers). With regard to stereoisomers, the compounds of formula (I) may have one or more asymmetric carbon atom and may occur as racemates, racemic mixtures and as individual enantiomers or diastereomers. All such isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of a compound of formula (I) can be present in racemic or enantiomerically enriched, for example the (R)-, (S)- or (R,S)-configuration. In certain embodiments, each asymmetric atom has at least 50 enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans- (E)-form.

Accordingly, as used herein a compound of formula (I) can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

The invention includes unlabeled forms as well as isotopically labeled forms of compounds of formula (I). Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Furthermore, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Representative Embodiments

Various embodiments of the invention are described herein. It will be recognized that features specified in each embodiment may be combined with other specified features to provide further embodiments.

In one embodiment of the present invention $R^1$ is optionally substituted $C_{1-4}$ alkyl.

In another embodiment $R^1$ is substituted methyl or substituted ethyl.

In another embodiment $R^1$ is $C_{1-4}$ alkyl, in particular methyl, substituted with an optionally substituted 5 membered heteroaryl, In particular, $R^1$ is $C_{1-4}$ alkyl, particularly methyl, substituted by one 2- or 3-thienyl, 2-, 4-, or 5-imidazolyl, 2-, 4-, or 5-thiazolyl, or 2-, 4-, or 5-oxazolyl each of which is optionally substituted with one or two substituents as described in formula (I). More particular, $R^1$ is $C_{1-4}$ alkyl, particularly methyl, substituted with one 2- or 3-thienyl, 2-, 4-, or 5-imidazolyl, 2-, 4-, or 5-thiazolyl, or 2-, 4-, or 5-oxazolyl optionally substituted with one halo group.

In another embodiment $R^1$ is $C_{1-4}$ alkyl substituted by one $C_{3-5}$ cycloalkyl, such as cyclopentyl. In particular $R^1$ is methyl substituted by one $C_{3-5}$ cycloalkyl, such as cyclopentyl.

In another embodiment $R^1$ is $C_{1-4}$ alkyl, particularly methyl or ethyl, substituted by optionally substituted phenyl. In particular, $R^1$ is $C_{1-4}$ alkyl, particularly methyl or ethyl, substituted by phenyl, said phenyl ring being optionally substituted with one halo group. In another embodiment $R^1$ is ethyl optionally substituted by an optionally substituted phenyl.

In another embodiment of the present invention $R^2$ is $R^3$—$C_{1-2}$alkylene-C(O)—. Suitably, $R^2$ is $R^3$—$C_{1-2}$alkylene-C(O)— wherein $R^3$ is optionally substituted phenyl, optionally substituted pyridinyl, or optionally substituted indolyl. More suitably, $R^2$ is $R^3$—$C_{1-2}$alkylene-C(O)— wherein $R^3$ is optionally substituted phenyl, optionally substituted pyridinyl, or optionally substituted indolyl, wherein said phenyl, pyridinyl, and indolyl are each optionally substituted with one to three substitutents each independently selected from the group consisting of: halo and hydroxy.

In another embodiment of the present invention $R^2$ is $R^3$—$C_{1-2}$alkylene-S(O)$_2$— wherein $R^3$ is phenyl.

In another embodiment of the present invention $R^2$ is $R^3$-ethylene-C(O)—, $R^3$-methylene-S(O)$_2$—, or $R^3$—$C_{1-2}$methylene-COO—.

In another embodiment of the present invention $R^a$ is H or $C_{1-3}$ alkyl and $R^b$ is H or $C_{1-3}$ alkyl. In another embodiment $R^a$ and $R^b$ are both H.

Enumerated Embodiments

Embodiment 1

A compound according to formula (I)

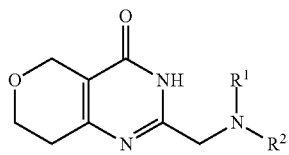

wherein:

$R^1$ is hydrogen or $C_{1-4}$ haloalkyl, or $C_{1-4}$ alkyl optionally substituted with one substituent selected from the group consisting of: hydroxy, cyano, $C(O)R^a$, $C_{3-5}$ cycloalkyl, optionally substituted phenyl, and optionally substituted 5-6 membered heteroaryl, wherein said phenyl and 5-6 member heteroaryl are each optionally substituted with one or two substituents each independently selected from the group consisting of: halo, hydroxy, $C_{1-3}$ alkyl, $C_{1-3}$ alkoxy, and cyano;

$R^2$ is $R^3$—$C_{1-2}$alkylene-C(O)—, $R^3$—$C_{1-2}$alkylene-S(O)$_2$—, or $R^3$—$C_{1-2}$alkylene-COO—;

$R^3$ is optionally substituted phenyl, optionally substituted 6 membered heteroaryl, or optionally substituted indolyl, wherein said phenyl, heteroaryl and indolyl are each optionally substituted with one to three substitutents each independently selected from the group consisting of: halo, hydroxy, cyano, nitro, $C_{1-6}$ alkyl, $C_{1-6}$ alkoxy, $C_{1-6}$ haloalkyl, $C(O)R^a$, $COOR^a$, $NR^aR^b$, $NHC(O)R^a$, and $C(O)NR^aR^b$;

$R^a$ is H or $C_{1-6}$ alkyl; and $R^b$ is H or $C_{1-6}$ alkyl; or a pharmaceutically acceptable salt thereof.

Embodiment 2

The compound according to embodiment 2 wherein $R^1$ is optionally substituted $C_{1-4}$ alkyl; or a pharmaceutically acceptable salt thereof.

Embodiment 3

The compound according to embodiment 1 or 2 wherein $R^1$ is substituted methyl or substituted ethyl; or a pharmaceutically acceptable salt thereof.

Embodiment 4

The compound according to any one of embodiments 1-3 wherein $R^1$ is methyl substituted by an optionally substituted 5 membered heteroaryl; or a pharmaceutically acceptable salt thereof.

Embodiment 5

The compound according to any one of embodiments 1-3 wherein $R^1$ is ethyl substituted by an optionally substituted phenyl; or a pharmaceutically acceptable salt thereof.

Embodiment 6

The compound according to any one of embodiments 1-5 wherein $R^2$ is $R^3$-ethylene-C(O)—, $R^3$-methylene-S(O)$_2$—, or $R^3$—$C_{1-2}$methylene-COO—; or a pharmaceutically acceptable salt thereof.

Embodiment 7

The compound according to any one of embodiments 1-5 wherein $R^2$ is $R^3$—$C_{1-2}$alkylene-C(O)—; or a pharmaceutically acceptable salt thereof.

Embodiment 8

The compound according to any one of embodiments 1-7 wherein $R^3$ is optionally substituted phenyl, optionally substituted pyridinyl, or optionally substituted indolyl; or a pharmaceutically acceptable salt thereof.

Embodiment 9

The compound according to embodiment 8 wherein the optionally substituted phenyl, optionally substituted pyridinyl, or optionally substituted indolyl are each optionally substituted with one to three substitutents each independently selected from the group consisting of: halo and hydroxy; or a pharmaceutically acceptable salt thereof.

General Synthetic Procedures

The compounds of the present invention may be made by a variety of methods, including standard chemistry. Illustrative general synthetic methods are set out below and specific compounds of the invention as prepared are given in the Examples.

The compounds of formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of formula (I).

Those skilled in the art will recognize if a stereocenter exists in the compounds of formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, "Stereochemistry of Organic Compounds" by E. L. Eliel, S. H. Wilen, and L. N. Mander (Wiley-interscience, 1994).

The compounds described herein may be made from commercially available starting materials or synthesized using known organic, inorganic, and/or enzymatic processes.

Scheme 1

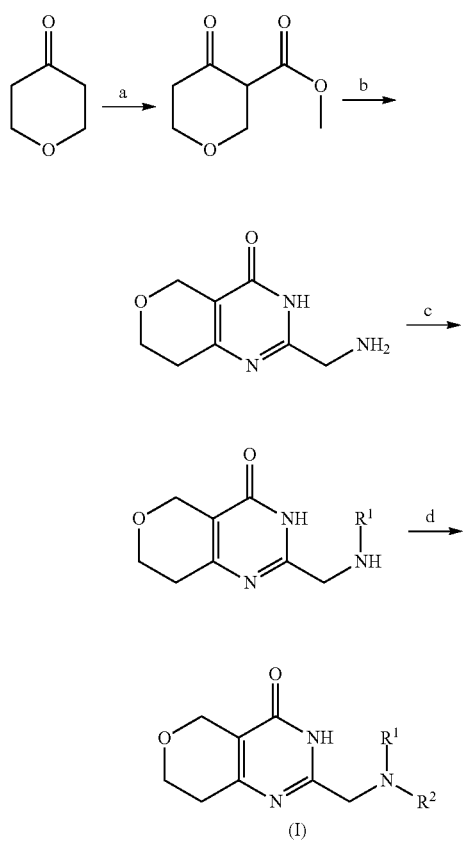

a) KOtBu, CO(OMe)$_2$; b) i. Benzyl 2-amino-2-iminoethylcarbamate hydrochloride. NaOEt, EtOH ii. H$_2$, Pd/C; c) R$^1$—CHO, SiCNBH$_3$, AcOH, EtOH; d) R$^2$SO$_2$Cl, TEA, DCM or R$^2$CO$_2$Cl, TEA, DCM or R$^2$CO$_2$H, EDCl, HOBt, TEA, DCM Substituted 2-aminomethyl-3,5,7,8-tetrahydro-pyrano[4,3-d]pyrimidin-4-ones can be prepared via a variety of methods, including methods that begin with the treatment of tetrahydropyran-4-one with potassium tert-butoxide (KOtBu) in methyl carbonate. Formation of the pyrimidinone ring is accomplished via reaction with an appropriate amidine, such as 2-amino-acetamidine under basic conditions, such as an alkoxide base, such as sodium ethoxide in a suitable solvent, such as ethanol. Hydrogenolysis of the Cbz protecting group reveals a primary amine that may be further elaborated via reductive amination, alkylation, acylation and/or sulfonylation.

Scheme 2

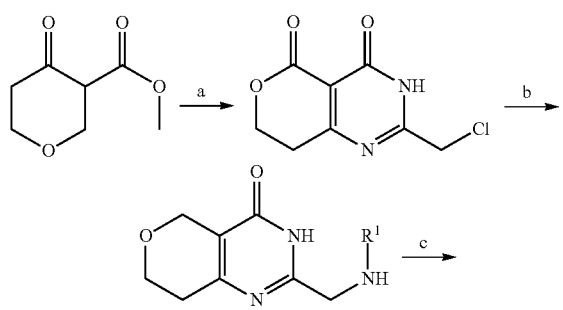

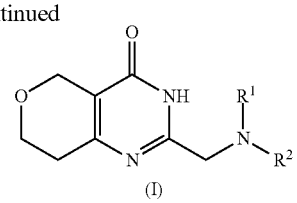

a) TEA, 2-chloroacetamidine, MeOH; b) i. BocNH R$^1$, NaH, THF or DMF ii. HCl, dioxane, MeOH; c) R$^2$SO$_2$Cl, TEA, DCM or R$^2$CO$_2$Cl, TEA, DCM or R$^2$CO$_2$H, EDCl, HOBt, TEA, DCM Substituted 2-aminomethyl-3,5,7,8-tetrahydro-pyrano[4,3-d]pyrimidin-4-ones can be prepared via a variety of methods. 2-Chloromethyl-3,5,7,8-tetrahydro-pyrano[4,3-d]pyrimidin-4-one is prepared by reacting intermediate 1 with 2-chloroacetamidine in the presence of a base, such as triethylamine, in a suitable solvent, such as methanol. Displacement of the chloride with a Boc-protected amine derivative is accomplished using a strong base, such as sodium hydride (NaH) in THF or DMF. Removal of the Boc group under acidic conditions, such as TFA or HCl in a suitable solvent, reveals the secondary amine which may be further elaborated via reductive amination, alkylation, acylation or sulfonylation.

Compositions

In another aspect, the present invention provides a pharmaceutical composition comprising a compound of formula (I), or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and/or
 e) absorbents, colorants, flavors and sweeteners.

Tablets may be either film coated or enteric coated according to methods known in the art.

Suitable compositions for oral administration include an effective amount of a compound of formula (I), or a pharmaceutically acceptable salt thereof, in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

Methods of Use

The compounds of formula (I) are tankyrase inhibitors and therefore may be useful in the treatment of diseases mediated by tanykyrase, including Wnt signaling related disorders and tankyrase 1 and 2 (TNKS/TNKS2) signaling related disorders.

Wnt signaling related disorders include diseases and conditions associated with aberrant Wnt signaling including but not limited to Wnt signaling-related cancers (e.g., colorectal cancer, malignant medulloblastoma and other primary CNS malignant neuroectodermal tumors, rhabdomyosarcoma, lung cancer, in particular small cell lung cancer, gut-derived tumors, including but not limited to cancer of the esophagus, stomach, pancreas, and biliary duct system, prostate and bladder cancers, and liver cancer); other, non-oncogenic proliferative diseases, such as proliferative skin disorders (e.g., psoriasis, dermatitis); osteoporosis; osteoarthritis; fibrosis; schizophrenia; vascular disease; cardiac disease; neurodegenerative diseases such as Alzheimer's disease; remyelination, including remyelination after brain and/or spinal code injury; and pulmonary fibrosis. Aberrant upregulation of Wnt signaling is associated with cancer, osteoarthritis, and polycystic kidney disease, while aberrant down regulation of Wnt signaling has been linked to osteoporosis, obesity, diabetes, and neuronal degenerative diseases.

Tankyrase signaling related disorders include diseases and conditions associated with aberrant tankyrase 1 and 2 signaling, including but not limited to cancer (e.g., leukemia, lymphoma, melanoma, multiple myeloma, lung, ovarian, and breast cancer) metabolic diseases and viral infection (e.g. Herpes Simplex Virus infection).

The term "a therapeutically effective amount" of a compound of the present invention refers to an amount of a compound of formula (I) that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of a compound of formula (I) when administered to a subject, is effective to (1) at least partially alleviating, inhibiting, preventing and/or ameliorating a condition, or a disorder or a disease (i) mediated by tankyrase, or (ii) associated with tankyrase activity, or (iii) characterized by activity (normal or abnormal) of tankyrase; or (2) reducing or inhibiting the activity of tankyrase or (3) reducing or inhibiting the expression of tankyrase. In another non-limiting embodiment, the term "a therapeutically effective amount" refers to the amount of a compound of formula (I) when administered to a cell, or a tissue, or a non-cellular biological material, or a medium, is effective to at least partially reducing or inhibiting the activity of tankyrase; or at least partially reducing or inhibiting the expression of tankyrase.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

Thus, as a further embodiment, the present invention provides the use of a compound of formula (I) or a pharmaceutically acceptable salt thereof, in therapy. In a further embodiment, the therapy is selected from a disease which may be treated by tankyrase inhibition. In one embodiment the disease is a Wnt signaling related disorder. In another embodiment the disease is a tankyrase signaling related disorder. In another embodiment, the disease is cancer, in particular a cancer selected from the group consisting of leukemia, melanoma, multiple myeloma, lymphoma, lung cancer, esophageal cancer, stomach cancer, pancreas cancer, biliary duct system cancer, ovarian cancer, breast cancer, prostate cancer, bladder cancer, colon cancer and liver cancer. In another embodiment, the disease is cancer, in particular, a cancer selected from the group consisting of leukemia, lung cancer, pancreas cancer, breast cancer and colon cancer. In another embodiment the disease is a cancer selected from the group consisting of colon, pancreas, and breast.

In another embodiment, the invention provides a use of a compound of formula (I), or a pharmaceutically acceptable salt thereof, in that manufacture of a medicament for the treatment of a disease mediated by tankyrase inhibition. In one embodiment the disease is a Wnt signaling related disorder. In another embodiment the disease is a tankyrase signaling related disorder. In another embodiment, the disease is cancer, in particular a cancer selected from the group consisting of leukemia, melanoma, multiple myeloma, lymphoma, lung cancer, esophageal cancer, stomach cancer, pancreas cancer, biliary duct system cancer, ovarian cancer, breast cancer, prostate cancer, bladder cancer, colon cancer and liver cancer. In another embodiment, the disease is cancer, in particular a cancer selected from the group consisting of leukemia, lung cancer, pancreas cancer, breast cancer and colon cancer. In another embodiment the disease is a cancer selected from the group consisting of colon, pancreas, and breast.

In another embodiment, the invention provides a method for the treatment of a disease mediated by tankyrase inhibition comprising administration of a therapeutically effective amount of a compound of formula (I) or a pharmaceutically acceptable salt thereof to a subject in need thereof. In one embodiment the disease is a Wnt signaling related disorder. In another embodiment the disease is a tankyrase signaling related disorder. In a further embodiment, the disease is cancer, in particular a cancer selected from the group consisting of leukemia, melanoma, multiple myeloma, lymphoma, lung cancer, esophageal cancer, stomach cancer, pancreas cancer, biliary duct system cancer, ovarian cancer, breast cancer, prostate cancer, bladder cancer, colon cancer and liver cancer. In another embodiment, the disease is cancer, in particular a cancer selected from the group consisting of leukemia, lung cancer, pancreas cancer, breast cancer and colon cancer. In another embodiment the disease is a cancer selected from the group consisting of colon, pancreas, and breast.

Combinations

The compounds of the present invention may be administered either simultaneously with, or before or after, one or more other therapeutic agent(s). The compounds of the present invention may be administered separately, by the same or different route of administration, or together in the same pharmaceutical composition as the other agents.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by TNKS inhibition. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by tankyrase inhibition wherein the medicament is prepared for administration with another therapeutic agent. The invention also provides the use of another therapeutic agent for treating a disease or condition mediated by tankyrase inhibition, wherein the medicament is administered with a compound of formula (I).

The invention also provides a compound of formula (I) for use in a method of treating a disease or condition mediated by tankyrase inhibition, wherein the compound of formula (I) is prepared for administration with another therapeutic agent. The invention also provides another therapeutic agent for use in a method of treating a disease or condition mediated by tankyrase inhibition, wherein the other therapeutic agent is prepared for administration with a compound of formula (I). The invention also provides a compound of formula (I) for use in a method of treating a disease or condition mediated by tankyrase inhibition, wherein the compound of formula (I) is administered with another therapeutic agent. The invention also provides another therapeutic agent for use in a method of treating a disease or condition mediated by tankyrase inhibition, wherein the other therapeutic agent is administered with a compound of formula (I).

The invention also provides the use of a compound of formula (I) for treating a disease or condition mediated by tankyrase inhibition, wherein the patient has previously (e.g. within 24 hours) been treated with another therapeutic agent. The invention also provides the use of another therapeutic agent for treating a disease or condition mediated by tankyrase inhibition, wherein the patient has previously (e.g. within 24 hours) been treated with a compound of formula (I).

In one embodiment, the other therapeutic agent is selected from the group of, but not limited to Hedgehog antagonists, PI3K inhibitors, MEK inhibitors, tyrosine kinase inhibitors, IAP (Inhibitors of Apoptosis Proteins) inhibitors, alkylating agents, anti-metabolites, microtubule inhibitors, telomerase inhibitors, PARP inhibitors, and RAF inhibitors.

An example of a Hedgehog antagonist is 2-chloro-N-[4-chloro-3-(2-pyridinyl)phenyl]-4-(methylsulfonyl)-benzamide (also known as GDC-0449, and described in PCT Publication No. WO 06/028958) and Erismodegib (also known as LDE225).

Some examples of PI3K inhibitors include: 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730) and 2-Methyl-2-[4-[3-methyl-2-oxo-β-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806).

An example of a Mitogen-activated protein kinase kinase (MEK) inhibitor is XL-518 (Cas No. 1029872-29-4, available from ACC Corp.).

Some examples of tyrosine kinase inhibitors include: Erlotinib hydrochloride (sold under the trademark Tarceva® by Genentech/Roche), Linifanib (N-[4-(3-amino-1H-indazol-4-yl)phenyl]-N'-(2-fluoro-5-methylphenyl)urea, also known as ABT 869, available from Genentech), sunitinib malate (sold under the trade name Sutent® by Pfizer), bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996), dasatinib (sold under the trade name Sprycel® by Bristol-Myers Squibb), pazopanib (also known as Armala™ sold under the trade name Votrient® by GlaxoSmithKline), and imatinib and imatinib mesylate (sold under the trade names Gilvec® and Gleevec® by Novartis).

An example of an IAP (Inhibitors of Apoptosis Proteins) inhibitor is (S)—N—((S)-1-Cyclohexyl-2-{(S)-2-[4-(4-fluoro-benzoyl)-thiazol-2-yl]-pyrrolidin-1-yl}-2-oxo-ethyl)-2-methylamino-propionamide (also known as LCL161 and described in PCT Publication No. WO2008/016893). Some examples of alkylating agents include: temozolomide (sold under the trade names Temodar® and Temodal® by Schering-Plough/Merck), dactinomycin (also known as actinomycin-D and sold under the trade name Cosmegen®), melphalan (also known as L-PAM, L-sarcolysin, and phenylalanine mustard, sold under the trade name Alkeran®), altretamine (also known as hexamethylmelamine (HMM), sold under the trade name Hexalen®), carmustine (sold under the trade name BiCNU®), bendamustine (sold under the trade name Treanda®), busulfan (sold under the trade names Busulfex® and Myleran®), carboplatin (sold under the trade name Paraplatin®), lomustine (also known as CCNU, sold under the trade name CeeNU®), cisplatin (also known as CDDP, sold under the trade names Platinol® and Platinol®-AQ), chlorambucil (sold under the trade name Leukeran®), cyclophosphamide (sold under the trade names Cytoxan® and Neosar®), dacarbazine (also known as DTIC, DIC and imidazole carboxamide, sold under the trade name DTIC-Dome®), altretamine (also known as hexamethylmelamine (HMM) sold under the trade name Hexalen®), ifosfamide (sold under the trade name Ifex®), procarbazine (sold under the trade name Matulane®), mechlorethamine (also known as nitrogen mustard, mustine and mechloroethamine hydrochloride, sold under the trade name Mustargen®), streptozocin (sold under the trade name Zanosar®), thiotepa (also known as thiophosphoamide, and TESPA and TSPA, sold under the trade name Thioplex®.

Some examples of Anti-metabolites include: claribine (2-chlorodeoxyadenosine, sold under the trade name Leustatin®), 5-fluorouracil (sold under the trade name Adrucil®), 6-thioguanine (sold under the trade name Purinethol®), pemetrexed (sold under the trade name Alimta®), cytarabine (also known as arabinosylcytosine (Ara-C), sold under the trade name Cytosar-U®), cytarabine liposomal (also known as Liposomal Ara-C, sold under the trade name DepoCytTm), decitabine (sold under the trade name Dacogen®), hydroxyurea (sold under the trade names Hydrea®, Droxia™ and Mylocel™), fludarabine (sold under the trade name Fludara®), floxuridine (sold under the trade name FUDR®), cladribine (also known as 2-chlorodeoxyadenosine (2-CdA) sold under the trade name Leustatin™), methotrexate (also known as amethopterin, methotrexate sodim (MTX), sold under the trade names Rheumatrex® and Trexall™), and pentostatin (sold under the trade name Nipent®).

Some examples of microtubule inhibitors are vinorelbine (sold under the trade name Navelbine®), vindesine (sold under the trade name Eldisine®), estramustine (sold under the trade name Emcyt®), vincristine (Oncovin®), triclabendazole (Egaten®), secnidazole, quinfamide, podophyllotoxin, mebendazole, griseofulvin, flubendazole, eribulin, colchicine, ciclobendazole, cabazitaxel, albendazole, and vinorelbine.

An example of a telomerase inhibitor is imetelstat.

Some examples of PARP inhibitors include: olaparib (from Astrazeneca), iniparib (also known as BSI-201), AGO14699 (Pfizer), veliparib (also known as ABT-888 from Enzo), and MK4827 (Merck).

Some examples of RAF inhibitors include: 2-Chloro-5-[2-Phenyl-5-(4-pyridinyl)-1H-imidazol-4-yl]phenol (also known as L-779450), 3-(dimethylamino)-N-[3-[(4-hydroxybenzoyl)amino]-4-methylphenyl]-benzamide (also known as ZM-336372) and sorafenib (marketed as Nexavar® by Bayer).

Intermediates and Examples

The following examples are intended to be illustrative only and not limiting in any way.

Abbreviations used are those conventional in the art or the following:

AcOH acetic acid
BOC tertiary butyl carboxy
C Celsius
d doublet
dd doublet of doublets
DCM dichloromethane
DIEA diethylisopropylamine
DME 1,4-dimethoxyethane
DMF N,N-dimethylformamide
DMSO dimethylsulfoxide
EtOAc ethyl acetate
EtOH ethanol
EDCL 1-ethyl-3-(3'-dimethylaminopropyl)carbodiimide
g gram
h hour(s)
HBTU 1-[bis(dimethylamino)methylene]-1H-benzotriazoliumhexafluorophosphate(1-) 3-oxide
HOBt 1-hydroxy-7-azabenzotriazole
HPLC high pressure liquid chromatography
IR infrared spectroscopy
kg kilogram
L liter
LCMS liquid chromatography and mass spectrometry
MTBE methyl tert butyl either
MeOH methanol
MS mass spectrometry
MW microwave
m multiplet
min minutes
mL milliliter(s)
m/z mass to charge ratio
nm nanometer
nM nanomolar
NMR nuclear magnetic resonance
Pd/C palladium on carbon
rac racemic
s singlet
SiCNBH$_3$
triplet
TEA triethylamine
TLC thin layer chromatography
TFA trifluoroacetic acid
THF tetrahydrofuran Intermediate 1: 4-Oxo-tetrahydro-pyran-3-carboxylic acid methyl ester

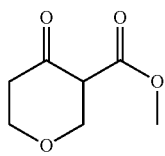

To a solution of tetrahydro-pyran-4-one (1.3 kg, 12.98 mol) and carbonic acid dimethyl ester (11.69 kg, 129.8 mol) was added solid potassium tert-butoxide (1.89 kg, 16.08 mol) in portions at −10° C. over 2 h under nitrogen protection. The suspension was stirred at room temperature 10 h after the addition. LCMS (215 nm) indicated that tetrahydro-pyran-4-one had been completely consumed. The reaction was acidified by HCl (2 N) to pH 6~7 and then the phases were separated. The organic phase was washed with water (3 L×2) and the combined aqueous phases were extracted with MTBE (2.5 L×2). The combined organic phase was concentrated under reduced pressure at 25° C. to remove most of MTBE. The residue was distilled out by oil pump (~200 Pa) at 74° C. to give the title compound as colorless oil (545 g, 26.3%). CHN analysis: calculated (results). C, 53.16; (53.10), H, 6.37; (6.245), N, 0.00; (0.00).

Intermediate 2: Benzyl 2-amino-2-iminoethylcarbamate hydrochloride

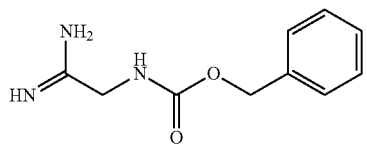 [SMILES: N=C(N)CNC(=O)OCc1ccccc1]

To a solution of benzyl cyanomethylcarbamate (65.4 g, 344 mmol) in methanol was added sodium methoxide (7.86 mL, 34.4 mmol, 25% in methanol). The mixture was stirred at ambient temperature for 24 h. Ammonium chloride (18.4 g, 344 mmol) was then added. The mixture was stirred at ambient temperature for another 24 h, and concentrated under reduced pressure. The resulting material was added into hexane/ethyl acetate (1:1) (240 mL) and ether (50 mL), stirred at ambient temperature for 1.5 h, then filtered to provide the title compound as a pale colored solid (78.8 g, 94% yield). $^1$H NMR (400 MHz, DMSO-d$_6$) δ 8.79 (br. s., 4H), 7.78 (t, J=5.5 Hz, 1H), 7.24-7.47 (m, 5H), 5.07 (s, 2H), 3.98 (d, J=5.5 Hz, 2H). MS m/z 208.2 (M+1), retention time=0.64 min.

Intermediate 3. Benzyl (4-oxo-4,5,7,8-tetrahydro-3H-pyrano[4,3-d]pyrimidin-2-yl)methylcarbamate

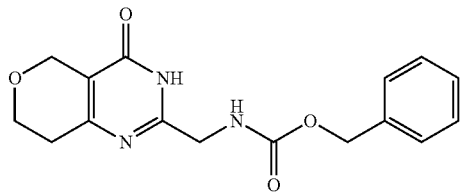 [SMILES: O=C(NCc1nc2c(c(=O)[nH]1)COCC2)OCc1ccccc1]

To a solution of methyl 4-oxotetrahydro-2H-pyran-3-carboxylate (51.1 g, 323 mmol) and benzyl 2-amino-2-iminoethylcarbamate hydrochloride (78.8 g, 323 mmol) in anhydrous ethanol was added sodium ethoxide (122 mL, 323 mmol, 21% in ethanol). The mixture was mechanically stirred, heated at reflux for 24 h, cooled down to ambient temperature, and filtered to give the title compound (55.6 g, 55% yield). $^1$H NMR (400 MHz, DMSO-d$_6$) δ 12.40 (br. s., 1H), 7.69 (t, J=5.8 Hz, 1H), 7.15-7.44 (m, 5H), 4.99-5.08 (m, 2H), 4.35 (s, 2H), 4.04-4.11 (m, 2H), 3.84 (t, J=5.3 Hz, 2H), 2.48-2.57 (m, 2H). MS m/z 316.2 (M+1), retention time=1.10 min.
Alternative Procedure
To benzyl 2-amino-2-iminoethylcarbamate (1.77 g, 8.54 mmol) in methanol (67.5 mL) was added methyl 4-oxotetrahydro-2H-pyran-3-carboxylate (1.35 g, 8.54 mmol) and potassium carbonate (3.54 g, 25.6 mmol). The reaction mixture was stirred 15 h at room temperature. The solution was filtered and concentrated under vacuum. Purification was accomplished on a 100 g Isco column with 0% to 10% methanol in dichloromethane over 20 column volumes to give title compound (1.63 g, 59% yield). Exact mass calculated for C$_{16}$H$_{17}$N$_3$O$_4$ 315.3. found 316.2 (ESI, M+H); $^1$H NMR (400

MHz, MeOD) δ ppm 7.17-7.46 (m, 5H) 5.11 (s, 2H) 4.47 (br. s., 2H) 4.22 (s, 2H) 3.92 (t, J=5.31 Hz, 2H) 2.65 (br. s., 2H).

Intermediate 4: 2-(Aminomethyl)-7,8-dihydro-3H-pyrano[4,3-d]pyrimidin-4(5H)-one

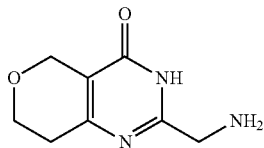 [SMILES: NCc1nc2c(c(=O)[nH]1)COCC2]

A solution of benzyl (4-oxo-4,5,7,8-tetrahydro-3H-pyrano[4,3-d]pyrimidin-2-yl)methylcarbamate (55.5 g, 176 mmol) in methanol (4 L) was degassed several times under nitrogen then palladium on carbon (1.87 g, 1.76 mmol, 10% on carbon) was added slowly under nitrogen atmosphere. The mixture was stirred under a hydrogen balloon at ambient temperature until TLC showed complete consumption of starting material. Filtration through a pad of Celite and evaporation of solvent provided the title compound (32 g, >99% yield). $^1$H NMR (400 MHz, CD$_3$OD) δ 4.49 (s, 2H), 3.93 (t, J=5.5 Hz, 2H), 3.77 (s, 2H), 2.66 (t, J=5.5 Hz, 2H). MS m/z 182.2 (M+1), retention time=0.39 min.

Alternative Procedure

To benzyl (4-oxo-4,5,7,8-tetrahydro-3H-pyrano[4,3-d]pyrimidin-2-yl)methylcarbamate (1.63 g, 51.7 mmol) in methanol (70 mL) was added 10% palladium hydroxide (726 mg, 0.52 mmol) and the mixture was stirred under 1 atm of H$_2$ for 4 h. The solution was filtered through celite and concentrated under vacuum to give 2-(aminomethyl)-7,8-dihydro-3H-pyrano[4,3-d]pyrimidin-4(5H)-one (707 mg, 75% yield). $^1$H NMR (400 MHz, DMSO-d$_6$) δ ppm 4.34 (s, 2H) 3.83 (t, J=5.56 Hz, 2H) 3.54 (s, 2H) 2.54 (t, J=5.56 Hz, 2H).

Intermediate 5: 2-Chloro-acetamidine

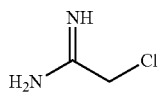

Sodium (18.3 g, 0.795 mol) was completely dissolved in 2 L of MeOH at 25° C. and stirred for 1 hour. To the solution was then added chloro-acetonitrile (600 g, 7.95 mol) dropwise in 1 hour under the protection of N$_2$. After being stirred at about 20° C. for an additional hour, NH$_4$Cl (514 g, 8.73 mol) was added in portions over 45 minutes (the solution turned to yellow and then red, and then a black liquid was obtained), the reaction mixture was then allowed to stir at 15-20° C. for 16 hours. After filtration, the filtrate was concentrated to give a residue, which was triturated with MTBE (1 L×2) to give the title compound as a black solid (988 g, 96%).

Intermediate 6: 2-Chloromethyl-3,5,7,8-tetrahydro-pyrano[4,3-d]pyrimidin-4-one

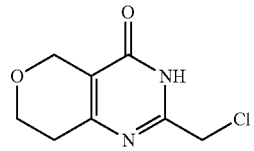 [SMILES: O=c1[nH]c(CCl)nc2c1COCC2]

A mixture of crude 4-oxo-tetrahydro-pyran-3-carboxylic acid methyl ester (1780 g, 11 mol) and NEt$_3$ (830 g, 8.2 mol) in MeOH (3560 mL) was cooled to 0° C. under N$_2$. A solution of 2-chloro-acetamidine (567 g, 4.4 mol) in 890 mL of MeOH was added dropwise over 50 minutes. The reaction mixture was stirred at 0° C. for 30 minutes and then at about 20° C. for 16 hours. LCMS at 215 nm and TLC (DCM:MeOH=10:1) analysis showed that most of 4-oxo-tetrahydro-pyran-3-carboxylic acid methyl ester was consumed. The mixture was then filtered and concentrated to give black oil, which was subsequently purified by flash column chromatography on silica gel and eluted with DCM to give yellow solid/oil mixture, which was further triturated with MTBE (~1200 mL) and H$_2$O: CH$_3$CN: EA=1:1:2 (~600 mL) to give the title compound as a white solid (318 g). MS m/z 201.2 (M+H). CHN analysis: calculated (results). C, 47.89; (47.95), H, 4.52; (4.401), N, 13.96; (13.76).

Intermediate 7: 2-{[1(Thiophen-2-ylmethyl)-amino]-methyl}-3,5,7,8-tetrahydro-pyrano[4,3-d]pyrimidin-4-one

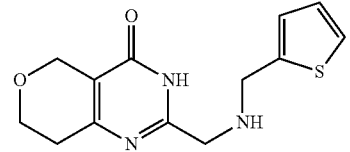 [SMILES: O=c1[nH]c(CNCc2cccs2)nc2c1COCC2]

A mixture of thiophene-2-carbaldehyde (0.021 mL, 0.22 mmol), 2-(aminomethyl)-7,8-dihydro-3H-pyrano[4,3-d]pyrimidin-4(5H)-one (40 mg, 0.22 mmol), and cyanoborohydride (240 mg, 0.24 mmol, 1 mmol/g) in ethanol (1 mL) was stirred at ambient temperature for 10 minutes. Acetic acid (0.013 mL, 0.22 mmol) was then added, and the mixture was stirred at ambient temperature for another 5 minutes. The reaction mixture was concentrated in vacuo and purified via flash column chromatography (ethyl acetate:hexane, 10:90 to 100:0, methanol: dichloromethane, 1:99 to 10:90) to provide the title compound (30 mg, 49% yield). m/z 278.1 (M+1), retention time=0.89 min.

Alternative Procedure

To 2-(aminomethyl)-7,8-dihydro-3H-pyrano[4,3-d]pyrimidin-4(5H)-one (100 mg, 0.552 mmol) in methylene chloride (5 mL) was added thiophene-2-carbaldehyde (62 mg, 0.552 mmol), sodium triacetoxyborohydride (351 mg, 1.66 mmol) and drop of acetic acid. The solution was stirred for 4 hr. The solvent was remover under vacuum, and the crude product was loaded on a Isco 12 g column. Elution with 0% to 10% methanol in methylene chloride over 15 column volumes afforded the title compound (95 mg, 61% yield). Exact mass calculated for C$_{13}$H$_{15}$N$_3$O$_2$S 277.3. found 278.2 (ESI, M+H); $^1$H NMR (400 MHz, MeOD) δ ppm 7.58 (d, J=5.05 Hz, 1H) 7.33 (d, J=3.03 Hz, 1H) 7.07-7.16 (m, 1H) 4.63 (s, 2H) 4.47 (s, 2H) 4.24 (s, 2H) 3.94 (t, J=5.56 Hz, 2H) 2.73 (t, J=5.56 Hz, 2H).

Example 1

N-((4-Oxo-4,5,7,8-tetrahydro-3H-pyrano[4,3-d]pyrimidin-2-ylmethyl)-3-phenyl-N-(thiophen-2-ylmethyl)propanamide

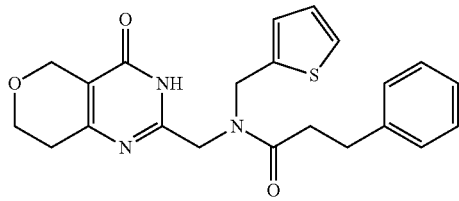 [SMILES: O=C(CCc1ccccc1)N(Cc1nc2c(c(=O)[nH]1)COCC2)Cc1cccs1]

To a solution of N-((4-oxo-4,5,7,8-tetrahydro-3H-pyrano[4,3-d]pyrimidin-2-yl)methyl)-3-phenyl-N-(thiophen-2-ylmethyl)propanamide (95 mg, 0.34 mmol) in methylene chloride (3 mL) was added triethylamine (143 μL, 1.028 mmol) and 3-phenylpropanoyl chloride (58 mg, 0.34 mmol) and the solution was stirred 4 hr. Purification was accomplished on an Isco 12 g column with 1% to 10% methanol in methylene chloride over 12 column volumes. The resulting partial purified product was taken up in DMSO and purified on a Sunfire C18-5 μm (19×100 mm) column. The mobile phase was 10% to 90% acetonitrile in water (0.1% TFA) to give title compound (39 mg, 28% yield). Exact mass calculated for $C_{22}H_{23}N_3O_3S$ 409.5. found 410.6 (ESI, M+H); $^1$H NMR (400 MHz, MeOD) δ ppm 7.09-7.39 (m, 5H) 6.79-7.00 (m, 2H) 4.77 (s, 1H) 4.35-4.49 (m, 4H) 3.79-3.98 (m, 2H) 3.35 (s, 1H) 2.81-3.01 (m, 3H) 2.73 (t, J=7.33 Hz, 1H) 2.49-2.68 (m, 2H).

The compounds in Table 1 were prepared by a method similar to the one described for the preparation of Example 1. As is appreciated by those skilled in the art, these analogous examples may involve variations in synthetic procedure.

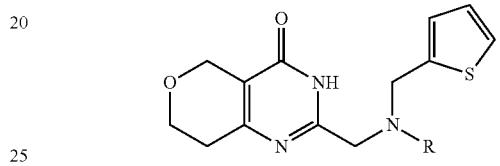

TABLE 1

| Example | R$^2$ | $^1$H NMR (400 MHz, CDCl$_3$) δ ppm | LCMS [RT (min)] |
|---|---|---|---|
| 2: 3-(4-Fluorophenyl)-N-(4-oxo-3,5,7,8-tetrahydro-4H-pyrano[4,3-d]pyrimidin-2-ylmethyl)-N-thiophen-2-ylmethyl-propionamide | ![structure] | 7.23-7.33 (m, 1 H), 7.11-7.22 (m, 2 H), 6.92-7.05 (m, 3 H), 6.88 (d, J = 3.0 Hz, 1 H), 4.70 (s, 2 H), 4.58 (s, 2 H), 4.42 (s, 2 H), 3.95 (t, J = 5.5 Hz, 2 H), 3.03 (t, J = 7.3 Hz, 2 H), 2.82 (t, J = 7.5 Hz, 2 H), 2.65 (t, J = 5.5 Hz, 2 H) | HRMS calculated for C$_{22}$H$_{22}$FN$_3$O$_3$S 428.1444, found (ESI, [M + H]$^+$), 428.1454 1.29 min |
| 3: 3-(1H-Indol-3-yl)-N-(4-oxo-3,5,7,8-tetrahydro-4H-pyrano[4,3-d]pyrimidin-2-ylmethyl)-N-thiophen-2-ylmethyl-propionamide | ![structure] | 11.51 (br. s., 1 H), 8.64 (br. s., 1 H), 7.46 (d, J = 7.5 Hz, 1 H), 7.12-7.34 (m, 2 H), 6.91-7.12 (m, 3 H), 6.81-6.91 (m, 1 H), 6.78 (d, J = 3.0 Hz, 1 H), 4.63 (s, 2 H), 4.43 (s, 2 H) 4.26 (s, 2 H), 3.63 (t, J = 5.5 Hz, 2 H), 3.13 (t, J = 6.8 Hz, 2 H), 2.90 (t, J = 6.8 Hz, 2 H), 2.43 (br. s., 2 H) | HRMS calculated for C$_{24}$H$_{24}$N$_4$O$_3$S 449.1647, found (ESI, [M + H]$^+$), 449.1650 4.94 min |
| 4: 3-(2-Fluorophenyl)-N-(4-oxo-3,5,7,8-tetrahydro-4H-pyrano[4,3-d]pyrimidin-2-ylmethyl)-N-thiophen-2-ylmethyl-propionamide | ![structure] | 10.49 (br. s., 1 H), 7.15-7.34 (m, 3 H), 6.86-7.15 (m, 4 H), 4.72 (s, 2 H), 4.58 (s, 2 H), 4.38-4.48 (m, 2 H), 3.95 (t, J = 5.5 Hz, 2 H), 3.09 (t, J = 7.8 Hz, 2 H), 2.86 (t, J = 7.5 Hz, 2 H), 2.57-2.72 (m, H) | HRMS calculated for C$_{22}$H$_{22}$FN$_3$O$_3$S 428.1444, found (ESI, [M + H]$^+$), 428.1439 5.21 min |
| 5: 3-(3-Fluorophenyl)-N-((4-oxo-4,5,7,8-tetrahydro-3H-pyrano[4,3-d]pyrimidin-2-yl)methyl)-N-(thiophen-2-ylmethyl)propanamide | ![structure] | 10.66 (br. s., 1 H), 7.20-7.38 (m, 2 H), 6.84-7.07 (m, 5 H), 4.72 (s, 2 H), 4.57 (s, 2 H), 4.44 (s, 2 H), 3.95 (t, J = 5.5 Hz, 2 H), 3.05 (t, J = 7.5 Hz, 2 H), 2.85 (t, J = 7.5 Hz, 2 H), 2.54-2.76 (m, 2 H) | HRMS calculated for C$_{22}$H$_{22}$FN$_3$O$_3$S 428.1444, found (ESI, [M + H]$^+$), 428.1454. 5.23 min |

TABLE 1-continued

| Example | R² | ¹H NMR (400 MHz, CDCl₃) δ ppm | LCMS [RT (min)] |
|---|---|---|---|
| 6: 3-(2-Hydroxy-phenyl)-N-(4-oxo-3,5,7,8-tetrahydro-4H-pyrano[4,3-d]pyrimidin-2-ylmethyl)-N-thiophen-2-ylmethyl-propionamide | 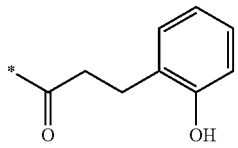 | 10.91 (br. s., 1 H), 8.21 (br. s., 1 H), 7.08-7.33 1 H), 6.93-7.08 (m, 2 H), 6.63-6.93 (m, 4 H), 4.54 (s, 2 H), 4.48 (s, 2 H), 4.37 (s, 2 H), 3.86 (t, J = 5.5 Hz, 2 H), 2.94-3.07 (m, 2 H), 2.78-2.94 (m, 2 H), 2.52-2.63 (m, 2 H) | HRMS calculated for $C_{22}H_{23}N_3O_4S$ 426.1488, found (ESI, [M + H]⁺), 426.1481 4.61 min |
| 7: 3-(3-Hydroxy-phenyl)-N-(4-oxo-3,5,7,8-tetrahydro-4H-pyrano[4,3-d]pyrimidin-2-ylmethyl)-N-thiophen-2-ylmethyl-propionamide | 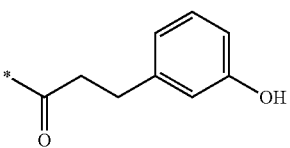 | 10.78 (br. s., 1 H), 7.23 (d, J = 5.0 Hz, 1 H), 7.17 (t, J = 7.8 Hz, 1 H), 7.10 (br. s., 1 H), 6.86-6.98 (m, 1 H), 6.74 (t, J = 6.8 Hz, 4 H), 4.56 (d, J = 18.1 Hz, 4 H), 4.46 (s, 2 H), 3.94 (t, J = 5.5 Hz, 2 H), 2.96-3.15 (m, 2 H), 2.79-2.91 (m, 2 H), 2.63 (t, J = 5.5 Hz, 2 H), 1.67 (s, 2 H) | HRMS calculated for $C_{22}H_{23}N_3O_4S$ 426.1488, found (ESI, [M + H]⁺), 426.1494 4.31 min |
| 8: 3-(4-Hydroxy-phenyl)-N-(4-oxo-3,5,7,8-tetrahydro-4H-pyrano[4,3-d]pyrimidin-2-ylmethyl)-N-thiophen-2-ylmethyl-propionamide | 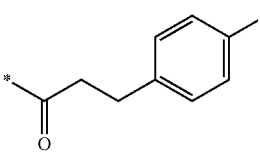 | 11.17 (br. s., 1 H), 7.27-7.29 (m, 1 H), 7.04 (m, J = 7.5 Hz, 2 H), 6.93-7.00 (m, 1 H), 6.89 (d, J = 3.0 Hz, 1 H), 6.72 (m, J = 8.0 Hz, 2 H), 4.71 (br. s., 2 H), 4.54 (br. s., 2 H), 4.44 (s, 2 H), 3.95 (t, J = 5.3 Hz, 2 H), 2.97 (t, J = 7.0 Hz, 2 H), 2.83 (t, J = 7.0 Hz, 2 H), 2.67 (br. s., 2 H). | HRMS calculated for $C_{22}H_{23}N_3O_4S$ 426.1488, found (ESI, [M + H]⁺), 426.1493 4.18 min |
| 9: N-((4-Oxo-4,5,7,8-tetrahydro-3H-pyrano[4,3-d]pyrimidin-2-yl)methyl)-1-phenyl-N-(thiophen-2-ylmethyl)methane-sulfonamide | 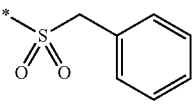 | 7.35-7.44 (m, 3 H), 7.32 (d, J = 4.0 Hz, 1 H), 7.22 (d, J = 5.5 Hz, 2 H), 7.04 (d, J = 3.0 Hz, 1 H), 6.93-7.01 (m, 1 H), 4.45-4.55 (m, 4 H), 4.37 (s, 2 H), 3.92 (t, J = 5.5 Hz, 2 H), 3.84 (s, 2 H), 2.61 (t, J = 5.5 Hz, 2 H) | HRMS calculated for $C_{20}H_{21}N_3O_4S_2$ 432.1052, found (ESI, [M + H]⁺), 432.1051 1.26 min |
| 10: 2-Phenyl-ethanesulfonic acid (4-oxo-3,5,7,8-tetrahydro-4H-pyrano[4,3-d]pyrimidin-2-ylmethyl)-thiophen-2-ylmethyl-amide | 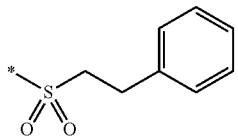 | 7.39-7.53 (m, 4 H), 7.32 (d, J = 7.0 Hz, 2 H), 7.20 (d, J = 3.0 Hz, 1 H), 7.07-7.16 (m, 1 H), 4.80 (s, 2 H), 4.70 (s, 2 H), 4.43 (s, 2 H), 4.09 (t, J = 5.5 Hz, 2 H), 3.39-3.55 (m, 2 H), 3.19-3.39 (m, 2 H), 2.79 (t, J = 5.5 Hz, 2 H) | HRMS calculated for $C_{21}H_{23}N_3O_4S_2$ 446.1208, found (ESI, [M + H]⁺), 446.1198 5.51 min |
| 11: N-((4-Oxo-4,5,7,8-tetrahydro-3H-pyrano[4,3-d]pyrimidin-2-yl)methyl)-3-(pyridin-4-yl)-N-(thiophen-2-ylmethyl)propanamide | 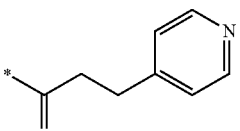 | MeOD) δ 8.66-8.80 (m, 2 H) 7.90-8.17 (m, 2 H) 6.70-6.89 (m, 1 H) 5.02-5.20 (m, 1 H) 4.73-4.83 (m, 2 H) 4.59-4.73 (m, 2 H) 4.15 (s, 1 H) 3.91-4.12 (m, 2 H) 3.35 (t, J = 6.32 Hz, 1 H) 3.09-3.29 (m, 2 H) 3.04 (br. s., 1 H) 2.76-2.96 (m, 1 H | Exact mass calculated for $C_{21}H_{22}N_4O_3S$ 410.3, found 411.3 (ESI, M + H) |

TABLE 1-continued

| Example | R² | ¹H NMR (400 MHz, CDCl₃) δ ppm | LCMS [RT (min)] |
|---|---|---|---|
| 12: N-((4-Oxo-4,5,7,8-tetrahydro-3H-pyrano[4,3-d]pyrimidin-2-yl)methyl)-3-(pyridin-4-yl)-N-(thiophen-2-ylmethyl)propanamide | *―CH₂CH₂-(pyridin-3-yl) (structure) | MeOD) δ 8.76-8.87 (m, 1 H) 8.72 (d, J = 5.05 Hz, 1 H) 8.52-8.68 (m, 1 H) 7.95-8.16 (m, 1 H) 6.90-7.05 (m, 1 H) 6.74-6.90 (m, 1 H) 4.90-5.16 (m, 2 H) 4.72-4.80 (m, 2 H) 4.55-4.72 (m, 2 H) 3.88-4.13 (m, 2 H) 2.99-3.29 (m, 5 H) 2.70-2.96 (m, 2 H) | Exact mass calculated for C₂₁H₂₂N₄O₃S 410.3, found 411.3 (ESI, M + H) |

Example 13

N-Cyclopentylmethyl-N-(4-oxo-3,5,7,8-tetrahydro-4H-pyrano[4,3-d]pyrimidin-2-ylmethyl)-3-phenylpropionamide

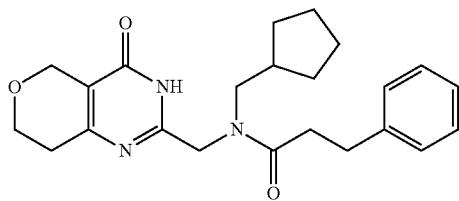 [SMILES: O=C(CCc1ccccc1)N(Cc1nc2c(c(=O)[nH]1)COCC2)CC1CCCC1]

Step 1. Intermediate 8: 2-[(Cyclopentylmethyl-amino)-methyl]-3,5,7,8-tetrahydro-yrano[4,3-d]pyrimidin-4-one

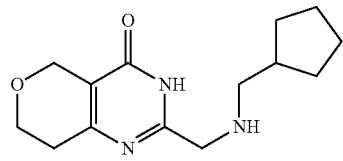 [SMILES: O=c1[nH]c(CNCC2CCCC2)nc2c1COCC2]

A mixture of cyclopentanecarbaldehyde (0.047 mL, 0.44 mmol), 2-(aminomethyl)-7,8-dihydro-3H-pyrano[4,3-d]pyrimidin-4(5H)-one (80 mg, 0.44 mmol), and siliabond cyanoborohydride (486 mg, 0.49 mmol, 1 mmol/g) in acetic acid (0.150 mL, 2.65 mmol) and DMF (1 mL) was microwave at 150° C. for 5 minutes. After filtration the solvent was evaporated under reduced pressure, and the residue was purified via HPLC to provide the title compound (35 mg, 30% yield). ¹H NMR (400 MHz, CD₃OD) δ 4.45-4.54 (m, 2H), 3.93 (t, J=5.8 Hz, 2H), 3.76 (s, 2H), 2.58-2.72 (m, 4H), 2.06-2.20 (m, 1H), 1.75-1.91 (m, 2H), 1.52-1.74 (m, 4H), 1.23 (dd, J=12.0, 7.5 Hz, 2H). Retention time=0.89 min.

Step 2

To a solution of 2-[(cyclopentylmethyl-amino)-methyl]-3,5,7,8-tetrahydro-yrano[4,3-d]pyrimidin-4-one (35 mg, 0.13 mmol) in dichloromethane (1 mL) was added 3-phenylpropanoyl chloride (20 μL, 0.13 mmol) and then triethylamine (56 μL, 0.40 mmol) at 0° C. The mixture was then allowed to slowly reach ambient temperature and stirred for 24 h. The mixture concentrated in vacuo and purified via HPLC to provide the title compound.

The compounds in Table 2 were prepared by a method similar to the one described for the preparation of Example 13. As is appreciated by those skilled in the art, these analogous examples may involve variations in synthetic procedure.

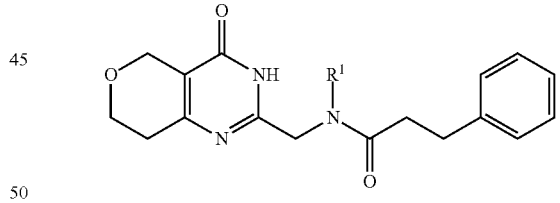

TABLE 2

| Example | R¹ | ¹H NMR (400 MHz, CDCl₃) δ ppm | LCMS RT (min) |
|---|---|---|---|
| 13: Cyclopentylmethyl-N-(4-oxo-3,5,7,8-tetrahydro-4H-pyrano[4,3-d]pyrimidin-2-ylmethyl)-3-phenylpropionamide | cyclopentylmethyl (structure) | 10.71 (br. s. 1 H), 6.94-7.19 (m, 5 H), 4.38 (s, 2 H), 4.22 (s, 2 H), 3.76 (t, J = 5.5 Hz, 2 H), 3.06 (d, J = 7.5 Hz, 2 H), 2.83 (t, J = 7.8 Hz, 2 H), 2.37-2.58 (m, 4 H), 1.95 (ddd, J = 14.8, 7.8, 7.5 Hz, 1 H), 1.23-1.52 (m, 6 H), 0.77-0.98 (m, 2 H) | HRMS calculated for C₂₃H₂₉N₃O₃ 396.2287, found (ESI, [M + H]⁺), 396.2289 5.63 min |

TABLE 2-continued

| Example | R¹ | ¹H NMR (400 MHz, CDCl₃) δ ppm | LCMS RT (min) |
|---|---|---|---|
| 14: N-(2-Fluorobenzyl)-N-((4-oxo-4,5,7,8-tetrahydro-3H-pyrano[4,3-d]pyrimidin-2-yl)methyl)-3-phenylpropanamide | 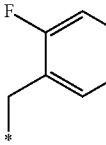 | 10.71 (br. s., 1 H), 7.26-7.36 (m, 2H), 7.15-7.26 (m, 3 H), 6.90-7.15 (m, 3 H), 4.48-4.65 (m, 4 H) 4.40 (s, 2 H), 3.93 (t, J = 5.5 Hz, 2 H), 3.05 (t, J = 7.5 Hz, 2 H), 2.81 (t, J = 7.5 Hz, 2 H), 2.60 (t, J = 5.3 Hz, 2 H) | HRMS calculated for $C_{24}H_{24}FN_3O_3$ 422.1880, found (ESI, [M + H]⁺), 422.1879 5.30 min |
| 15: N-Ethyl-N-((4-oxo-4,5,7,8-tetrahydro-3H-pyrano[4,3-d]pyrimidin-2-yl)methyl)-3-phenylpropanamide |  | 6.55-6.78 (m, 5 H), 4.02 (s, 2 H), 3.82 (s, 2 H), 3.40 (t, J = 5.3 Hz, 2 H), 2.82 (q, J = 6.5 Hz, 2 H), 2.37-2.56 (m, 2 H), 2.01-2.22 (m, 4 H), 0.45-0.64 (m, 3 H). | HRMS calculated for $C_{19}H_{23}N_3O_3$ 342.1818, found (ESI, [M + H]⁺), 342.1811 4.36 min |
| 16: N-Isopropyl-N-((4-oxo-4,5,7,8-tetrahydro-3H-pyrano[4,3-d]pyrimidin-2-yl)methyl)-3-phenylpropanamide |  | 10.85 (br. s., 1 H), 7.15-7.37 (m, 5 H), 4.58 (s, 2 H), 4.36 (s, 2 H), 4.04-4.20 (m, 1 H), 3.96 (t, J = 5.6 Hz, 2 H), 3.04 (t, J = 7.8 Hz, 2 H), 2.76 (t, J = 7.8 Hz, 2 H), 2.67 (tt, J = 5.5, 1.8 Hz, 2 H), 1.14 (d, J = 6.7 Hz, 6 H) | HRMS calculated for $C_{20}H_{25}N_3O_3$ 356.1974, found (ESI, [M + H]⁺), 356.1968 4.74 min |
| 17: N-(3,3-Dimethyl-2-oxobutyl)-N-((4-oxo-4,5,7,8-tetrahydro-3H-pyrano[4,3-d]pyrimidin-2-yl)methyl)-3-phenylpropanamide | 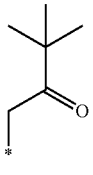 | 7.04-7.34 (m, 5 H), 4.59 (s, 2 H), 4.42 (s, 2 H), 4.29 (s, 2 H), 3.95 (t, J = 5.5 Hz, 2 H), 2.96 (ddd, J = 19.4, 7.7, 7.5 Hz, 2 H), 2.60-2.73 (m, 2 H), 2.55 (t, J = 7.8 Hz, 1 H), 2.42 (t, J = 7.8 Hz, 1 H), 1.16-1.35 (m, 9 H) | HRMS calculated for $C_{23}H_{29}N_3O_4$ 412.2236, found (ESI, [M + H]⁺), 412.2232 5.06 min |
| 18: N-((4-Oxo-4,5,7,8-tetrahydro-3H-pyrano[4,3-d]pyrimidin-2-yl)methyl)-3-phenyl-N-(thiophen-3-ylmethyl)propanamide | 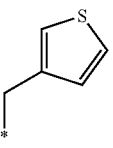 | MeOD) δ ppm 7.43 (dd, J = 5.05, 3.03 Hz, 1 H) 7.11-7.39 (m, 6 H) 6.88-7.02 (m, 1 H) 4.74 (s, 1 H) 4.67 (s, 1 H) 4.44-4.56 (m, 3 H) 4.41 (s, 1 H) 3.95 (q, J = 5.56 Hz, 2 H) 2.95-3.09 (m, 2 H) 2.77-2.95 (m, 2 H) 2.58-2.74 (m, 2 H) | Exact mass calculated for $C_{22}H_{23}N_3O_3S$ 409.5, found 410.6 (ESI, M + H) |
| 19: N-((4-Oxo-4,5,7,8-tetrahydro-3H-pyrano[4,3-d]pyrimidin-2-yl)methyl)-3-phenyl-N-(thiazol-2-ylmethyl)propanamide | 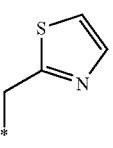 | MeOD) δ ppm 7.62-7.76 (m, 1 H) 7.01-7.27 (m, 5 H) 5.15 (s, 1 H) 4.94 (s, 1 H) 4.61 (s, 2 H) 4.42-4.54 (m, 2 H) 3.81-4.05 (m, 2 H) 2.82-3.00 (m, 2 H) 2.68-2.79 (m, 3 H) 2.64-2.68 (m, 1 H) 2.56 (t, J = 5.56 Hz, 1 H). | Exact mass calculated for $C_{21}H_{22}N_4O_3S$ 410.5, found 411.2 (ESI, M + H) |
| 20: N-(Oxazol-2-ylmethyl)-N-((4-oxo-4,5,7,8-tetrahydro-3H-pyrano[4,3-d]pyrimidin-2-yl)methyl)-3-phenylpropanamide | 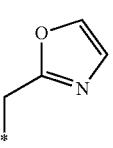 | MeOD) δ ppm 7.09-7.29 (m, 6 H) 4.91 (s, 1 H) 4.79 (s, 1 H) 4.63 (s, 1 H) 4.57 (s, 1 H) 4.43-4.54 (m, 2 H) 3.84-3.99 (m, 2 H) 2.91 (t, J = 7.33 Hz, 2 H) 2.81 (t, J = 7.33 Hz, 1 H) 2.56-2.69 (m, 3 H) | Exact mass calculated for $C_{21}H_{22}N_4O_4$ 394.3, found 395.3 (ESI, M + H) |
| 21: N-((5-Chlorothiophen-2-yl)methyl)-N-((4-oxo-4,5,7,8-tetrahydro-3H-pyrano[4,3-d]pyrimidin-2-yl)methyl)-3-phenylpropanamide | 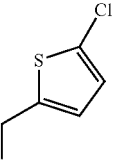 | MeOD) δ ppm 7.12-7.38 (m, 6 H) 6.74-6.84 (m, 1 H) 4.71 (s, 1 H) 4.43-4.57 (m, 4 H) 3.97 (dt, J = 9.09, 5.56 Hz, 2 H) 3.02 (t, J = 7.58 Hz, 2 H) 2.92 (t, J = 7.07 Hz, 1 H) 2.81 (t, J = 7.58 Hz, 1 H) 2.56-2.74 (m, 2 H). | Exact mass calculated for $C_{22}H_{22}ClN_3O_3S$ 443.1, found 444.1 (ESI, M + H) |

TABLE 2-continued

| Example | R[1] | $^1$H NMR (400 MHz, CDCl$_3$) δ ppm | LCMS RT (min) |
|---|---|---|---|
| 22: N-((4-Oxo-4,5,7,8-tetrahydro-3H-pyrano[4,3-d]pyrimidin-2-yl)methyl)-3-phenyl-N-(thiazol-5-ylmethyl)propanamide | 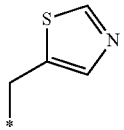 | MeOD) δ 7.73-7.88 (m, 1 H) 7.06-7.35 (m, 5 H) 5.00 (s, 1 H) 4.82 (s, 1 H) 4.46 (d, J = 8.59 Hz, 4 H) 3.77-4.02 (m, 2 H) 2.82-3.03 (m, 3 H) 2.74 (t, J = 7.33 Hz, 1 H) 2.59-2.69 (m, 2 H) 2.54 (t, J = 5.56 Hz, 1 H) | Exact mass calculated for C$_{22}$H$_{22}$N$_4$O$_3$S 410.5, found 411.2 (ESI, M + H) |

Intermediate 9: 2-((2-(tert-Butyldimethylsilyloxy)ethylamino)methyl)-7,8-dihydro-3H-pyrano[4,3-d]pyrimidin-4(5H)-one

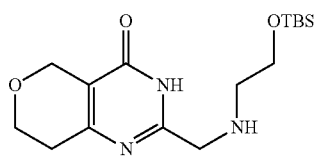 [SMILES: CC(C)(C)[Si](C)(C)OCCNCc1nc2c(c(=O)[nH]1)COCC2]

To a mixture of 2-(aminomethyl)-7,8-dihydro-3H-pyrano[4,3-d]pyrimidin-4(5H)-one (50 mg, 0.28 mmol) and 2-(tert-butyldimethylsilyloxy)acetaldehyde (53 uL, 0.28 mmol) in DMF (1 mL) was added siliabond cyanoborohydride (300 mg, 0.30 mmol, 1 mmol/g) and acetic acid (0.158 mL, 2.8 mmol). The mixture was heated via microwave at 150° C. for 5 minutes, concentrated in vacuo and the resulting material was purified via HPLC to provide the title compound (10 mg, 11% yield). $^1$H NMR (400 MHz, CDCl$_3$) δ 4.51 (s, 2 H), 3.87 (t, J=5.5 Hz, 2H), 3.71 (s, 2H), 3.58-3.68 (m, 2H), 2.62 (ddd, J=14.7, 5.3, 5.1 Hz, 4H), 0.82 (s, 9H), 0.00 (s, 6H). Retention time=1.52 min.

Example 23

N-(2-Hydroxy-ethyl)-N-(4-oxo-3,5,7,8-tetrahydro-4H-pyrano[4,3-d]pyrimidin-2-ylmethyl)-3-phenyl-propionamide

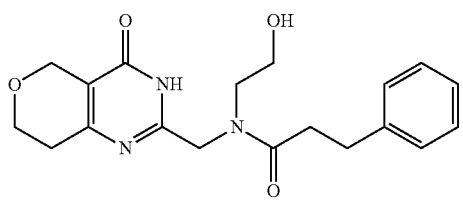 [SMILES: O=C(CCc1ccccc1)N(CCO)Cc1nc2c(c(=O)[nH]1)COCC2]

To a solution of 2-((2-(tert-butyldimethylsilyloxy)ethylamino)methyl)-7,8-dihydro-3H-pyrano[4,3-d]pyrimidin-4(5H)-one (10 mg, 0.029 mmol) in dichloromethane (0.1 mL) was added 3-phenylpropanoyl chloride (4.4 μL, 0.029 mmol) and then triethylamine (12 μL, 0.088 mmol) at 0° C. The mixture was stirred at 0° C. to ambient temperature for 24 h. Tetra-N-butylammonium fluoride (29 μL, 0.029 mmol, 1 M in THF) was added and the reaction was stirred at ambient temperature for 1 h. The mixture was concentrated in vacuo then purified via prep thin layer chromatography to provide the title compound (2.3 mg, 22% yield). $^1$H NMR (400 MHz, CDCl$_3$) δ 7.18-7.34 (m, 3H), 7.14 (d, J=7.5 Hz, 2H), 4.56 (s, 2H), 4.38 (s, 2H), 3.95 (t, J=5.5 Hz, 2H), 3.65-3.82 (m, 2H), 3.58 (t, J=4.5 Hz, 2H), 2.87-3.06 (m, 2H), 2.81 (t, J=7.5 Hz, 2H), 2.67 (br. s., 2H). HRMS calculated for C$_{19}$H$_{23}$N$_3$O$_4$ 358.1767. found (ESI, [M+H]$^+$), 358.1767. Retention time=0.99 min.

Example 24

(S)—N-((4-Oxo-4,5,7,8-tetrahydro-3H-pyrano[4,3-c]pyrimidin-2-yl)methyl)-1-phenyl-N-(1-phenylethyl)methanesulfonamide

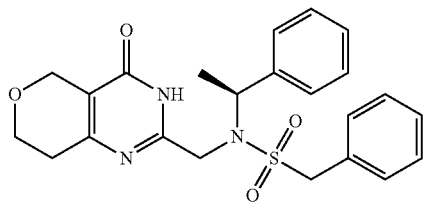 [SMILES: C[C@@H](c1ccccc1)N(Cc1nc2c(c(=O)[nH]1)COCC2)S(=O)(=O)Cc1ccccc1]

To (S)-2-((1-phenylethylamino)methyl)-7,8-dihydro-3H-pyrano[4,3-d]pyrimidin-4(5H)-one (25 mg, 0.088 mmol) and DIEA (92 μL, 0.527 mmol) in methylene chloride (2 mL) was added phenylmethanesulfonyl chloride (50 mg, 0.263 mmol) and the reaction solution was stirred for 3 hr. The reaction was quenched with 7 N ammonia in methanol (4 mL) and stirred for an additional 3 hr. The reaction was diluted with methylene chloride (20 mL) and absorbed onto silica gel (25 mg). Purification was accomplished on a Biotage SNAP-10 g column with 1% to 16% methanol in methylene chloride over 12 column volumes. The resulting partial purified product was taken up in DMSO and purified on a Sunfire C18-5 μm (19× 100 mm) column. The mobile phase was 10% to 65% acetonitrile in water (0.1% TFA). Lyophilization afforded the title compound (10.5 mg 27% yield). Exact mass calculated for C$_{23}$H$_{25}$N$_3$O$_4$S 439.5. found 440.3 (ESI, M+H); $^1$H NMR (400 MHz, dichloromethane-d$_2$) δ ppm 7.35-7.46 (m, 5H) 7.22-7.35 (m, 5H) 5.33-5.39 (m, 1H) 4.31-4.46 (m, 4H) 3.95-4.08 (m, 2H) 3.76-3.90 (m, 2H) 2.41-2.62 (m, 2H) 1.54 (d, J=7.07 Hz, 3H).

Example 25

(R)—N-((4-Oxo-4,5,7,8-tetrahydro-3H-pyrano[4,3-d]pyrimidin-2-yl)methyl)-1-phenyl-N-(1-phenyl-ethyl)methanesulfonamide

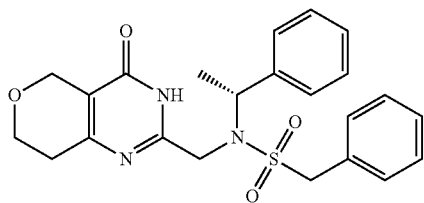 [SMILES: C[C@H](c1ccccc1)N(Cc1nc2c(c(=O)[nH]1)COCC2)S(=O)(=O)Cc1ccccc1]

Following the general methods described in Example 24, the title compound was prepared (26 mg, 67% yield) from (R)-2-((1-phenylethylamino)methyl)-7,8-dihydro-3H-pyrano[4,3-d]pyrimidin-4(5H)-one (25 mg, 0.088 mmol). Exact mass calculated for $C_{23}H_{25}N_3O_4S$ 439.5. found 440.3 (ESI, M+H); $^1H$ NMR (400 MHz, dichloromethane-$d_2$) δ ppm 7.35-7.46 (m, 5H) 7.22-7.35 (m, 5H) 5.33-5.39 (m, 1H) 4.31-4.46 (m, 4H) 3.95-4.08 (m, 2H) 3.76-3.90 (m, 2H) 2.41-2.62 (m, 2H) 1.54 (d, J=7.07 Hz, 3H).

Intermediate 10: 2-(((1H-Pyrrol-2-yl)methylamino)methyl)-7,8-dihydro-3H-pyrano[4,3-d]pyrimidin-4(5H)-one

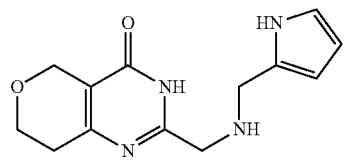 [SMILES: O=c1[nH]c(CNCc2ccc[nH]2)nc2c1COCC2]

Following general methods of intermediate 7, alternative procedure, the title compound was prepared (77 mg, 26% yield) from 1H-pyrrole-2-carbaldehyde (110 mg, 1.159 mmol). Exact mass calculated for $C_{13}H_{16}N_4O_2$ 260.3. found 261.2 (ESI, M+H).

Example 26

N-((1H-Pyrrol-2-yl)methyl)-3-(2-fluorophenyl)-N-((4-oxo-4,5,7,8-tetrahydro-3H-pyrano[4,3-d]pyrimidin-2-yl)methyl)propanamide

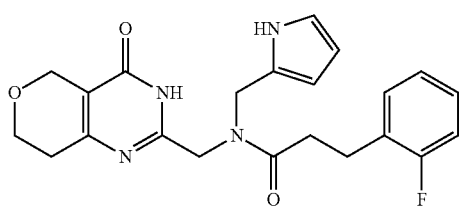 [SMILES: O=C(CCc1ccccc1F)N(Cc1ccc[nH]1)Cc1nc2c(c(=O)[nH]1)COCC2]

Following the general methods described in Example 1, the title compound was prepared (6 mg, 9% yield) from 2-(((1H-pyrrol-2-yl)methylamino)methyl)-7,8-dihydro-3H-pyrano[4,3-d]pyrimidin-4(5H)-one (40 mg, 0.154 mmol). Exact mass calculated for $C_{22}H_{23}FN_4O_3$ 410.5. found 411.2 (ESI, M+H); $^1H$ NMR (400 MHz, MeOD) δ7.14-7.32 (m, 3H) 6.93-7.13 (m, 3H) 6.71 (s, 1H) 6.02 (br. s., 1H) 5.95 (d, J=13.64 Hz, 1H) 4.67 (s, 2H) 4.58 (s, 1H) 4.36-4.51 (m, 5H) 3.85-3.98 (m, 3H) 2.80-3.07 (m, 5H) 2.52-2.80 (m, 5H).

Biological Assays and Data

Biochemical Assay to Determine Compound Inhibition of TNKS Enzyme Activity

The human tankyrase 1 PARP catalytic domain, TNKS1P, was cloned into a pDONR221 vector using the Invitrogen Gateway Technology. This entry clone was then subcloned into the destination vector pDEST20 to obtain the N-terminal Glutathione S-transferase (GST)-tagged fusion protein. GST-TNKS1P was then expressed in Sf21 cells using the Invitrogen baculovirus expression system (Invitrogen-Bac-to-Bac® Baculovirus Expression System, Version D). The protein was purified by a GSTrap column (GE Healthcare). The N-terminal GST-tagged tankyrase 2 protein PARP domain, TNKS2P, was cloned, expressed, and purified in a similar manner. Human PARP1 (Cat. No. 4668-100-01) and activated DNA (Cat. No. 4671-096-06) were purchased from Trevigen, Inc. PARP2 (Cat. No. ALX-201-064-C020) was purchased from Alexis Biochemical.

The autoparsylation activity of the TNKS 1/2 or PARP1/2 enzymes was measured by the liquid chromatography-mass spectrometry (LC/MS) detection of nicotinamide as readout. Compound activity in inhibiting the TNKS and PARP autoparsylation was evaluated by $IC_{50}$ measurements. In the compound screening assays, the reaction is composed of 5 μL of compound in β-point serial dilutions with concentrations ranging from 0.0086 to 18.75 μM, 20 nM of purified enzyme, and 250 μM of β-$NAD^+$ in the 1× Assay Buffer. After 60 min incubation at room temperature, the reactions were quenched by the addition of 10 μL of 5× quenching solution (20% formic acid and 500 nM [$d^4$]-nicotinamide in water). For the background control wells, 10 μL of the 5× quenching solution per well was added prior to the addition of β-$NAD^+$. The % Inhibition was calculated as: (Control−Sample)/(Control−Background)*100. "Control" is the average value of 8 wells without compound; and "Background" is the average of 8 wells mixed with 5× quenching solution measured prior to initiation of the reaction.

Examples 1-26 were tested in one or more of the above enzymatic assays, the results of which are given in Table 3.

TABLE 3

Enzymatic assay results

| Example | TNKS2 AP $IC_{50}$ (μM) | TNKS1 AP $IC_{50}$ (μM) | PARP1 $IC_{50}$ (μM) | PARP2 $IC_{50}$ (μM) |
| --- | --- | --- | --- | --- |
| 1 | 0.222 ± 0.008 | 1.15 ± 0.02 | | >19 |
| 2 | 0.078 ± 0.005 | 0.299 ± 0.026 | | |
| 3 | 1.58 ± 0.23 | 6.40 ± 0.24 | | |
| 4 | 0.064 ± 0.015 | 0.271 ± 0.045 | | |
| 5 | 0.284 ± 0.056 | 1.58 ± 0.014 | | |
| 6 | 0.766 ± 0.023 | 5.19 ± 0.227 | | |
| 7 | 0.178 ± 0.016 | 1.02 ± 0.003 | | >19 |
| 8 | 0.341 ± 0.003 | 1.42 ± 0.04 | | |
| 9 | 0.177 ± 0.067 | 1.16 ± 0.027 | | |
| 10 | 0.91 ± 0.11 | 5.12 ± 0.41 | | |
| 11 | 0.962 ± 0.013 | 4.17 ± 0.26 | | |
| 12 | 10.1 ± 3.1 | 14.6 ± 0.4 | | |
| 13 | 0.995 ± 0.094 | 4.78 ± 0.36 | | |
| 14 | 1.05 ± 0.05 | 5.61 ± 0.24 | | |
| 15 | 4.78 ± 0.4 | >19 | | |
| 16 | 5.39 ± 1.63 | >19 | | |
| 17 | 2.99 ± 0.036 | 17.1 ± 2.0 | | |
| 18 | 1.03 ± 0.07 | 5.17 ± 0.46 | 71 ± 18 | 10.4 ± 0.8 |
| 19 | 2.03 ± 0.04 | 11.4 ± 0.4 | | |

TABLE 3-continued

Enzymatic assay results

| Example | TNKS2 AP IC$_{50}$ (µM) | TNKS1 AP IC$_{50}$ (µM) | PARP1 IC$_{50}$ (µM) | PARP2 IC$_{50}$ (µM) |
|---|---|---|---|---|
| 20 | 1.70 ± 0.03 | 4.6 ± 0.2 | | |
| 21 | 0.318 ± 0.009 | 1.61 ± 0.11 | | |
| 22 | 3.48 ± 0.71 | 17.5 ± 1.0 | | |
| 23 | 2.68 ± 0.077 | 16.93 ± 0.02 | | |
| 24 | 3.12 ± 0.06 | 18.1 ± 1.9 | | |
| 25 | 1.85 ± 0.06 | 9.08 ± 0.76 | | |
| 26 | 0.235 ± 0.024 | 1.17 ± 0.12 | | |

Cellular Reporter Gene Assay to Determine Compound Inhibition of Wnt Signaling Activity Compound activity in inhibiting Wnt ligand-induced signaling was measured using a Wnt-responsive Super-TOp-Flash (STF) luciferase reporter gene assay in HEK293 cells. On day 1 of the assay, cells were plated at a density of 8000 cells per well of 384-well plate in 25 µl medium containing 5% fetal bovine serum (FBS). On the second day, 20 Wnt3A condition medium (CM) produced from mouse L cells was added to the cells to induce Wnt signaling, followed by addition of 5 µL of compounds each well in 10-point serial dilution. On the third day, the luciferase activity was measured by the Bright-Glo™ Luciferase Assay System following manufacture's protocol (Promega, E2620). The Inhibition was calculated as: (Maximum Wnt-induced signaling−Sample)/(Maximum Wnt-induced signaling−Background)*100. "Maximum Wnt-induced signaling" is the STF signal level induced by 20% Wnt3A CM without compound; and "Background" is the STF signal level without the addition of Wnt3A CM or compound.

Cellular ELISA Assay to Determine Compound Effect on Stabilizing the Axin2 Protein Compound activity in stabilizing the Axin2 protein was measured by Sandwich Enzyme-Linked Immuosorbent (ELISA) assay in the colorectal cell line SW480. 30,000 SW480 cells were seeded per well in 96-well plate and incubated overnight prior to compound treatment. Cells were then treated with compounds in 6-point dilution starting at 10 µM for 24 hrs. Cells were then washed with 100 µL of cold Phosphate Buffer Saline (PBS), and lysed in 125 µl of cold 1× lysis buffer (Cell Signaling Technology, 9803) supplemented with Protease inhibitor (Roche, 11836170) and Phosphatase inhibitors (Sigma, P2850, P5726). For the ELISA assay, anti Axin-2 capture antibody (Strategic Diagnostics) antibody was diluted to a concentration of 1 µg/ml (1:1000) in Carbonate Coating buffer, pH 9.2 (Sigma, C3041-50CAP). 100µ of the diluted anti Axin-2 capture antibody per well was then used to coat the 96-well ELISA plate (Thermo Electron Corp., MicroLite 1 flat bottom plate #7571) overnight at 4° C. Plates were then washed three times with 300 of wash solution, PBST20 (PBS+0.05% Tween), and blocked with 300 µl/well 1% BSA/PBS (BSA, Millipore Probumin #82-045-1) for 1.5 hours at room temperature while shaking gently. After blocking, plates were then washed three times with 300 of wash solution. 100 µL of prepared SW480 cell lysate was then added to each well and incubated at room temperature for 2 hours while shaking gently. After washing, 100 µL of Biotinylated anti-Axin2 antibody (CST, 2151) was added to each well and incubated room temperature for 2 hours. 100 µL of Streptavidin-HRP (R&D systems, DY998) diluted 1:200 in 1% BSA/PBS was then added in each well and incubate for 30 mins at R/T in the dark. Signal was detected by Chemiluminescence (Pierce SuperSignal ELISA Femto #3704), and measured on PerkinElmer Wallac 1420 plate reader.

Cellular Proliferation Assay to Determine Compound Inhibition of Cancer Cell Growth Non-small lung cancer ABC-1 cells were plated at 5000 cells per well in 96-well plates and treated with 8 serial compound dilutions starting from 10 µM as the highest concentration. Viable cells were measured after 3 days of compound treatment using the CellTiter-Glo assay (Promega, G7570). Assay was performed following the manufacture protocol. Excel XLfit 4 was used for plotting of the growth curves and calculation of IC$_{50}$ values. % growth following compound treatment was calculated as: (treated sample/(DMSO control)*100. IC$_{50}$ values are concentrations of the compound at which cell growth is inhibited by 50%.

Examples 1-26 were tested in one or more of the above cellular assays, the results of which are given in Table 4.

TABLE 4

Cellular assay results

| EXAMPLE | HEK293STF IC$_{50}$ (µM) | Axin AC$_{50}$ (µM) | ABC-1 IC$_{50}$ (µM) |
|---|---|---|---|
| 1 | 1.92 ± 0.62 | >10 | >10 |
| 2 | 0.483 ± 0.017 | 8.2 ± 0.3 | >10 |
| 3 | 9.31 ± 3.9 | | |
| 4 | 0.301 ± 0.055 | 4.1 ± 2.1 | 8.74 |
| 5 | 6.6 ± 1.5 | | |
| 6 | 3.77 ± 0.96 | | |
| 7 | 0.812 ± 0.046 | >10 | >10 |
| 8 | 1.35 ± 0.08 | | |
| 9 | 0.90 ± 0.23 | | |
| 10 | 2.43 ± 0.94 | | |
| 11 | 8.25 ± 0.51 | | |
| 12 | 41.0 ± 1.6 | | |
| 13 | 4.09 ± 1.29 | | |
| 14 | 4.09 ± 0.1 | | |
| 15 | >50 | | |
| 16 | 34.9 | | |
| 17 | 14.3 ± 1.0 | | |
| 18 | 8.54 ± 0.46 | | |
| 19 | 8.56 ± 0.42 | | |
| 20 | 14.3 ± 4.0 | | |
| 21 | 1.97 ± 0.56 | | |
| 22 | 18.2 ± 4.5 | | |
| 23 | >50 | | |
| 24 | 15.7 ± 0.8 | | |
| 25 | 23.2 ± 7.9 | | |
| 26 | 5.00 ± 0.72 | | |

What is claimed is:

1. A compound according to formula (I)

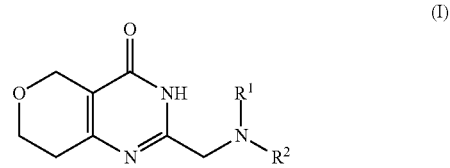

wherein:
  $R^1$ is hydrogen or $C_{1-4}$ haloalkyl, or $C_{1-4}$ alkyl optionally substituted with one substituent selected from the group consisting of: hydroxy, cyano, C(O)R$^a$, $C_{3-5}$ cycloalkyl, optionally substituted phenyl, and optionally substituted 5-6 membered heteroaryl,
    wherein said phenyl and 5-6 member heteroaryl are each optionally substituted with one or two substituents each independently selected from the group consisting of: halo, hydroxy, $C_{1-3}$ alkyl, $C_{1-3}$ alkoxy, and cyano;

R² is R³—C₁₋₂alkylene-C(O)—, R³—C₁₋₂alkylene-S(O)₂—, or R³—C₁₋₂alkylene-COO—;

R³ is optionally substituted phenyl, optionally substituted 6 membered heteroaryl, or optionally substituted indolyl, wherein said phenyl, heteroaryl and indolyl are each optionally substituted with one to three substitutents each independently selected from the group consisting of: halo, hydroxy, cyano, nitro, C₁₋₆ alkyl, C₁₋₆ alkoxy, C₁₋₆ haloalkyl, C(O)Rᵃ, COORᵃ, NRᵃRᵇ, NHC(O)Rᵃ, and C(O)NRᵃRᵇ;

Rᵃ is H or C₁₋₆ alkyl; and

Rᵇ is H or C₁₋₆ alkyl; or a pharmaceutically acceptable salt thereof.

2. The compound according to claim 1 wherein R¹ is optionally substituted C₁₋₄ alkyl; or a pharmaceutically acceptable salt thereof.

3. The compound according to claim 1 wherein R¹ is substituted methyl or substituted ethyl; or a pharmaceutically acceptable salt thereof.

4. The compound according to claim 1 wherein R¹ is methyl substituted by an optionally substituted 5 membered heteroaryl; or a pharmaceutically acceptable salt thereof.

5. The compound according to claim 1 wherein R¹ is ethyl substituted by an optionally substituted phenyl; or a pharmaceutically acceptable salt thereof.

6. The compound according to claim 1 wherein R² is R³-ethylene-C(O)—, R³-methylene-S(O)₂—, or R³—C₁₋₂ methylene-COO—; or a pharmaceutically acceptable salt thereof.

7. The compound according to claim 1 wherein R² is R³—C₁₋₂alkylene-C(O)—; or a pharmaceutically acceptable salt thereof.

8. The compound according to claim 1 wherein R³ is optionally substituted phenyl, optionally substituted pyridinyl, or optionally substituted indolyl; or a pharmaceutically acceptable salt thereof.

9. The compound according to claim 8 wherein the optionally substituted phenyl, optionally substituted pyridinyl, or optionally substituted indolyl are each optionally substituted with one to three substitutents each independently selected from the group consisting of: halo and hydroxy; or a pharmaceutically acceptable salt thereof.

10. The compound according to claim 9 wherein R¹ is C₁₋₄ alkyl, particularly methyl, substituted with one 2- or 3-thienyl, 2-, 4-, or 5-imidazolyl, 2-, 4-, or 5-thiazolyl, or 2-, 4-, or 5-oxazolyl optionally substituted with one halo group; or a pharmaceutically acceptable salt thereof.

11. The compound according to claim 1 which is:
N-((4-Oxo-4,5,7,8-tetrahydro-3H-pyrano[4,3-d]pyrimidin-2-yl)methyl)-3-phenyl-N-(thiophen-2-ylmethyl)propanamid;
3-(4-Fluoro-phenyl)-N-(4-oxo-3,5,7,8-tetrahydro-4H-pyrano[4,3-d]pyrimidin-2-ylmethyl)-N-thiophen-2-ylmethyl-propionamide;
3-(1H-Indol-3-yl)-N-(4-oxo-3,5,7,8-tetrahydro-4H-pyrano[4,3-d]pyrimidin-2-ylmethyl)-N-thiophen-2-ylmethyl-propionamid;
3-(2-Fluoro-phenyl)-N-(4-oxo-3,5,7,8-tetrahydro-4H-pyrano[4,3-d]pyrimidin-2-ylmethyl)-N-thiophen-2-ylmethyl-propionamide;
3-(3-Fluorophenyl)-N-((4-oxo-4,5,7,8-tetrahydro-3H-pyrano[4,3-d]pyrimidin-2-yl)methyl)-N-(thiophen-2-ylmethyl)propanamide;
3-(2-Hydroxy-phenyl)-N-(4-oxo-3,5,7,8-tetrahydro-4H-pyrano[4,3-d]pyrimidin-2-ylmethyl)-N-thiophen-2-ylmethyl-propionamide;
3-(3-Hydroxy-phenyl)-N-(4-oxo-3,5,7,8-tetrahydro-4H-pyrano[4,3-d]pyrimidin-2-ylmethyl)-N-thiophen-2-ylmethyl-propionamide;
3-(4-Hydroxy-phenyl)-N-(4-oxo-3,5,7,8-tetrahydro-4H-pyrano[4,3-d]pyrimidin-2-ylmethyl)-N-thiophen-2-ylmethyl-propionamide;
N-((4-Oxo-4,5,7,8-tetrahydro-3H-pyrano[4,3-d]pyrimidin-2-yl)methyl)-1-phenyl-N-(thiophen-2-ylmethyl)methanesulfonamide;
2-Phenyl-ethanesulfonic acid (4-oxo-3,5,7,8-tetrahydro-4H-pyrano[4,3-d]pyrimidin-2-ylmethyl)-thiophen-2-ylmethyl-amide;
N-((4-Oxo-4,5,7,8-tetrahydro-3H-pyrano[4,3-d]pyrimidin-2-yl)methyl)-3-(pyridin-4-yl)-N-(thiophen-2-ylmethyl)propanamide;
N-((4-Oxo-4,5,7,8-tetrahydro-3H-pyrano[4,3-d]pyrimidin-2-yl)methyl)-3-(pyridin-4-yl)-N-(thiophen-2-ylmethyl)propanamide;
N-Cyclopentylmethyl-N-(4-oxo-3,5,7,8-tetrahydro-4H-pyrano[4,3-d]pyrimidin-2-ylmethyl)-3-phenyl-propionamide;
Cyclopentylmethyl-N-(4-oxo-3,5,7,8-tetrahydro-4H-pyrano[4,3-d]pyrimidin-2-ylmethyl)-3-phenyl-propionamide;
N-(2-Fluorobenzyl)-N-((4-oxo-4,5,7,8-tetrahydro-3H-pyrano[4,3-d]pyrimidin-2-yl)methyl)-3-phenylpropanamide;
N-Ethyl-N-((4-oxo-4,5,7,8-tetrahydro-3H-pyrano[4,3-d]pyrimidin-2-yl)methyl)-3-phenylpropanamide;
N-Isopropyl-N-((4-oxo-4,5,7,8-tetrahydro-3H-pyrano[4,3-d]pyrimidin-2-yl)methyl)-3-phenylpropanamide;
N-(3,3-Dimethyl-2-oxobutyl)-N-((4-oxo-4,5,7,8-tetrahydro-3H-pyrano[4,3-d]pyrimidin-2-yl)methyl)-3-phenylpropanamide;
N-((4-Oxo-4,5,7,8-tetrahydro-3H-pyrano[4,3-d]pyrimidin-2-yl)methyl)-3-phenyl-N-(thiophen-3-ylmethyl)propanamide;
N-((4-Oxo-4,5,7,8-tetrahydro-3H-pyrano[4,3-d]pyrimidin-2-yl)methyl)-3-phenyl-N-(thiazol-2-ylmethyl)propanamide;
N-(Oxazol-2-ylmethyl)-N-((4-oxo-4,5,7,8-tetrahydro-3H-pyrano[4,3-d]pyrimidin-2-yl)methyl)-3-phenylpropanamide;
N-((5-Chlorothiophen-2-yl)methyl)-N-((4-oxo-4,5,7,8-tetrahydro-3H-pyrano[4,3-d]pyrimidin-2-yl)methyl)-3-phenylpropanamide;
N-((4-Oxo-4,5,7,8-tetrahydro-3H-pyrano[4,3-d]pyrimidin-2-yl)methyl)-3-phenyl-N-(thiazol-5-ylmethyl)propanamide;
N-(2-Hydroxy-ethyl)-N-(4-oxo-3,5,7,8-tetrahydro-4H-pyrano[4,3-d]pyrimidin-2-ylmethyl)-3-phenyl-propionamide;
(S)—N-((4-Oxo-4,5,7,8-tetrahydro-3H-pyrano[4,3-d]pyrimidin-2-yl)methyl)-1-phenyl-N-(1-phenylethyl)methanesulfonamide; or
(R)—N-((4-Oxo-4,5,7,8-tetrahydro-3H-pyrano[4,3-d]pyrimidin-2-yl)methyl)-1-phenyl-N-(1-phenylethyl)methanesulfonamide; or a pharmaceutically acceptable salt thereof.

12. A pharmaceutical composition comprising a compound according to claim 1, or a pharmaceutically acceptable salt thereof, and a pharmaceutically acceptable excipient or carrier.

13. A method for the treatment of cancer selected from the group consisting of colon, pancreas and breast comprising administration of a therapeutically effective amount of a compound according to claim 1, or a pharmaceutically acceptable salt thereof, to a subject in need thereof.

* * * * *